United States Patent
McKinnell et al.

(10) Patent No.: US 7,759,363 B2
(45) Date of Patent: *Jul. 20, 2010

(54) BENZIMIDAZOLE-CARBOXAMIDE COMPOUNDS AS 5-HT$_4$ RECEPTOR AGONISTS

(75) Inventors: Robert Murray McKinnell, Half Moon Bay, CA (US); Roland Gendron, San Francisco, CA (US); Lan Jiang, Foster City, CA (US); Seok-ki Choi, Palo Alto, CA (US); Daniel D. Long, San Francisco, CA (US); Paul R. Fatheree, San Francisco, CA (US); Daniel Marquess, Half Moon Bay, CA (US)

(73) Assignee: Theravance, Inc., South San Francisco, CA (US)

( * ) Notice: Subject to any disclaimer, the term of this patent is extended or adjusted under 35 U.S.C. 154(b) by 1019 days.

This patent is subject to a terminal disclaimer.

(21) Appl. No.: 11/439,671

(22) Filed: May 24, 2006

(65) Prior Publication Data

US 2006/0270652 A1 Nov. 30, 2006

Related U.S. Application Data

(60) Provisional application No. 60/748,415, filed on Dec. 8, 2005, provisional application No. 60/684,466, filed on May 25, 2005, provisional application No. 60/684,478, filed on May 25, 2005.

(51) Int. Cl.
*A61K 31/4545* (2006.01)
*C07D 403/14* (2006.01)

(52) U.S. Cl. .................. 514/316; 546/186; 546/187; 546/190

(58) Field of Classification Search .......... 514/316; 546/186, 187, 190
See application file for complete search history.

(56) References Cited

U.S. PATENT DOCUMENTS

| | | | |
|---|---|---|---|
| 6,294,555 B1 | 9/2001 | Kato et al. | |
| 6,552,046 B2 * | 4/2003 | Druzgala et al. | 514/329 |
| 6,696,468 B2 | 2/2004 | Kato et al. | |
| 7,256,294 B2 | 8/2007 | Dalziel et al. | |
| 2007/0244157 A1 | 10/2007 | Dalziel et al. | |
| 2009/0209582 A1 * | 8/2009 | McKinnell et al. | 514/316 |

FOREIGN PATENT DOCUMENTS

| | | |
|---|---|---|
| ES | 2 154 605 A1 | 4/2001 |
| JP | 11001472 A2 | 1/1999 |
| JP | 20001122784 A2 | 5/2001 |
| JP | 2004-277319 * | 7/2004 |
| JP | 2004277318 | 10/2004 |
| JP | 2004277318 A2 | 10/2004 |
| JP | 2004277319 A2 | 10/2004 |
| JP | 2004277320 A2 | 10/2004 |
| WO | WO97/35860 * | 10/1997 |
| WO | WO 97/35860 A1 | 10/1997 |
| WO | WO 2004/026868 A1 | 4/2004 |
| WO | WO 2005/021539 A1 | 3/2005 |

OTHER PUBLICATIONS

Seddon "Pseudopolymorph . . . " Crystal growth & design v. 496) p. 1087 (2004) (2 pages from internet).*
Braga et al. "Making crystal . . . " Royal Soc. Chem. Chem commun. p. 3635-3645 (2005).*
U.S. Appl. No. 11/920,817, McKinnell et al.
U.S. Appl. No. 11/439,669, Dalziel et al.
Lopez-Rodriguez et al., "3-D-QSAR/CoMFA and Recognition Models of Benzimidazole Derivatives at the 5-HT$_4$ Receptor", Bioorganic & Medicinal Chemistry Letters, 11, pp. 2807-2811 (2001).
Lopez-Rodriguez et al., "Benzimidazole Derivates. Part 1: Synthesis and Structure-Activity Relationships of New Benzimidazole-4-carboxamides and Carboxylates as Potent and Selective 5-HT$_4$ Receptor Antagonists", Bioorganic & Medicinal Chemistry, 7, pp. 2271-2281 (1999).
Lopez-Rodriguez et al., "Benzimidazole Derivatives. 3. 3D-QSAR/CoMFA Model and Computational Simulation for the Recognition of 5-HT$_4$ Receptor Antagonists", J. Med. Chem., 45, pp. 4806-4815 (2002).
Lopez-Rodriguez et al., "Benzimidazone derivatives 4. The recognition of the voluminous substituent attached to the basic amino group of 5-HT$_4$ receptor antagonists", Journal of Computer-Aided Molecular Design, 17, pp. 515-524 (2003).
Lopez-Rodriguez et al., "Design and Synthesis of New Benzimidazole-Arylpiperazine Derivatives Acting as Mixed 5-HT$_{1A}$/5-HT$_3$ Ligands", Bioorganic & Medicinal Chemistry Letters, 13, pp. 3177-3180 (2003).

(Continued)

*Primary Examiner*—Celia Chang
(74) *Attorney, Agent, or Firm*—Jeffrey A. Hagenah; Roberta P. Saxon

(57) ABSTRACT

The invention relates to benzimidazole-carboxamide 5-HT$_4$ receptor agonist compounds of formula (I)

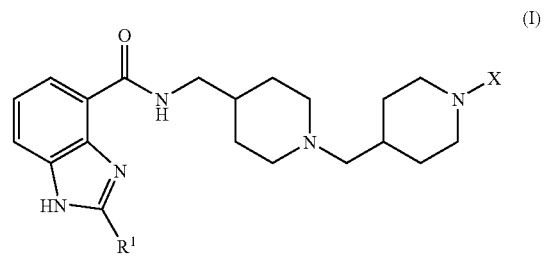

(I)

wherein $R^1$ and X are as defined in the specification, or a pharmaceutically acceptable salt or solvate or stereoisomer thereof. The invention also relates to pharmaceutical compositions comprising such compounds, methods of using such compounds to treat diseases associated with 5-HT$_4$ receptor activity, and processes and intermediates useful for preparing such compounds.

18 Claims, No Drawings

OTHER PUBLICATIONS

Lopez-Rodriguez et al., "Study of the bioactive conformation of novel 5-$HT_4$ receptor ligands: influence of an intramolecular hydrogen bond", Tetrahedron, 57, pp. 6745-6749 (2001).

Harada et al., "Novel N-(1-(1-Substituted 4-Piperidinylmethyl)-4-piperidinyl]benzamides as Potent Colonic Prokinetic Agents", Bioorganic & Medicinal Chemistry Letters 12, pp. 967-970 (2002).

* cited by examiner

BENZIMIDAZOLE-CARBOXAMIDE COMPOUNDS AS 5-HT$_4$ RECEPTOR AGONISTS

CROSS-REFERENCE TO RELATED APPLICATIONS

This application claims the benefit of U.S. Provisional Applications Nos. 60/684,466 and 60/684,478, filed on May 25, 2005, and 60/748,415, filed on Dec. 8, 2005, the disclosures of which are incorporated herein by reference in their entirety.

BACKGROUND OF THE INVENTION

1. Field of the Invention

The invention is directed to benzimidazole-carboxamide compounds which are useful as 5-HT$_4$ receptor agonists. The invention is also directed to pharmaceutical compositions comprising such compounds, methods of using such compounds for treating or preventing medical conditions mediated by 5-HT$_4$ receptor activity, and processes and intermediates useful for preparing such compounds.

2. State of the Art

Serotonin (5-hydroxytryptamine, 5-HT) is a neurotransmitter that is widely distributed throughout the body, both in the central nervous system and in peripheral systems. At least seven subtypes of serotonin receptors have been identified and the interaction of serotonin with these different receptors is linked to a wide variety of physiological functions. There has been, therefore, substantial interest in developing therapeutic agents that target specific 5-HT receptor subtypes.

In particular, characterization of 5-HT$_4$ receptors and identification of pharmaceutical agents that interact with them has been the focus of significant recent activity. (See, for example, the review by Langlois and Fischmeister, *J. Med. Chem.* 2003, 46, 319-344.) 5-HT$_4$ receptor agonists are useful for the treatment of disorders of reduced motility of the gastrointestinal tract. Such disorders include irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-HT$_4$ receptor agonist compounds may be used in the treatment of central nervous system disorders including cognitive disorders, behavioral disorders, mood disorders, and disorders of control of autonomic function.

Despite the broad utility of pharmaceutical agents modulating 5-HT$_4$ receptor activity, few 5-HT$_4$ receptor agonist compounds are in clinical use at present. Accordingly, there is a need for new 5-HT$_4$ receptor agonists that achieve their desired effects with minimal side effects. Preferred agents may possess, among other properties, improved selectivity, potency, pharmacokinetic properties, and/or duration of action.

SUMMARY OF THE INVENTION

The invention provides novel compounds that possess 5-HT$_4$ receptor agonist activity. Among other properties, compounds of the invention have been found to be potent and selective 5-HT$_4$ receptor agonists. In addition, preferred compounds of the invention have been found to exhibit favorable pharmacokinetic properties in an animal model which are predictive of good bioavailability upon oral administration.

Accordingly, the invention provides a compound of formula (I):

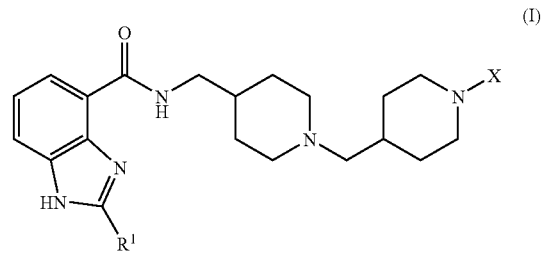

wherein:
R$^1$ is C$_{3-5}$alkyl, optionally substituted with —OH; and
X is selected from
(a) —C(O)OR$^2$ wherein R$^2$ is C$_{1-4}$alkyl or —(CH$_2$)$_n$-phenyl wherein n is 0 or 1;
(b) —C(O)R$^3$ wherein R$^3$ is selected from:
  phenyl, optionally substituted with 1, 2, or 3 substituents selected from C$_{1-4}$alkyl, halo, C$_{1-4}$alkoxy, —CF$_3$, —OCF$_3$, —OCHF$_2$, and —CN,
  C$_{1-5}$alkyl,
  C$_{4-5}$cycloalkyl, and
  —(CH$_2$)$_m$-A wherein m is 0 or 1 and A is selected from amino, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, and 2,4-dimethylisoxazolyl;
(c) —C(O)NR$^4$R$^5$ wherein R$^4$ is hydrogen or C$_{1-3}$alkyl, and R$^5$ is phenyl optionally substituted with 1, 2, or 3 substituents selected from C$_{1-4}$alkyl, halo, C$_{1-4}$alkoxy, —CF$_3$, —OCF$_3$, and —OCHF$_2$;
(d) —C(O)C(R$^6$R$^7$)R$^8$ wherein R$^6$ is hydrogen or C$_{1-3}$alkyl and R$^7$ is hydrogen, —OH, or C$_{1-3}$alkyl; or R$^6$ and R$^7$ taken together form oxo or —(CH$_2$)$_2$—; and R$^8$ is phenyl or cyclohexyl, wherein phenyl or cyclohexyl are optionally substituted with 1, 2, or 3 substituents selected from C$_{1-4}$alkyl, halo, C$_{1-4}$alkoxy, —CF$_3$, —OCF$_3$, —OCHF$_2$, and —CN;
(e) —C(O)C(HR$^9$)OR$^{10}$ wherein R$^9$ is hydrogen or C$_{1-3}$alkyl, and R$^{10}$ is phenyl optionally substituted with 1, 2, or 3 substituents selected from C$_{1-4}$alkyl, halo, C$_{1-4}$alkoxy, —CF$_3$, —OCF$_3$, and —OCHF$_2$; and
(f) —S(O)$_2$R$^{11}$ wherein R$^{11}$ is selected from C$_{1-3}$alkyl, —CH$_2$-phenyl, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, 2,4-dimethylisoxazolyl, and phenyl optionally substituted with 1, 2, or 3 substituents selected from C$_{1-4}$alkyl, halo, C$_{1-4}$alkoxy, —CF$_3$, —OCF$_3$, —OCHF$_2$, and —CN;
or a pharmaceutically-acceptable salt or solvate or stereoisomer thereof.

The invention also provides a pharmaceutical composition comprising a compound of the invention and a pharmaceutically-acceptable carrier.

In another aspect, the invention provides a method of treating a disease or condition associated with 5-HT$_4$ receptor activity, e.g. a disorder of reduced motility of the gastrointestinal tract, the method comprising administering to the mammal, a therapeutically effective amount of a compound of the invention.

Further, the invention provides a method of treating a disease or condition associated with 5-HT$_4$ receptor activity in a mammal, the method comprising administering to the mammal, a therapeutically effective amount of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate or stereoisomer thereof, as a research tool for studying a biological system or sample or for discovering new 5-HT$_4$ receptor agonists, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with 5-HT$_4$ receptor activity, e.g. a disorder of reduced motility of the gastrointestinal tract, in a mammal.

DETAILED DESCRIPTION OF THE INVENTION

The invention provides novel benzimidazole-carboxamide 5-HT$_4$ receptor agonists of formula (I), or pharmaceutically-acceptable salts or solvates or stereoisomers thereof. The following substituents and values are intended to provide representative examples of various aspects of this invention. These representative values are intended to further define such aspects and are not intended to exclude other values or limit the scope of the invention.

In a specific aspect of the invention, $R^1$ is $C_{3-5}$alkyl, optionally substituted with —OH.

In another specific aspect, $R^1$ is $C_{3-5}$alkyl.

In other specific aspects, $R^1$ is $C_{3-4}$alkyl; or $R^1$ is isopropyl or tert-butyl.

In another specific aspect, $R^1$ is isopropyl.

In yet other specific aspects, $R^1$ is 1-hydroxy-1-methylethyl, or 2-hydroxy-1-methylethyl.

In a specific aspect, X is —C(O)OR$^2$ wherein $R^2$ is $C_{1-4}$alkyl or —(CH$_2$)$_n$-phenyl wherein n is 0 or 1.

In another specific aspect, X is —C(O)OR$^2$ wherein $R^2$ is $C_{1-3}$alkyl or phenyl.

In other specific aspects, X is —C(O)OR$^2$ wherein $R^2$ is methyl or phenyl, or wherein $R^2$ is methyl.

In a specific aspect, X is —C(O)R$^3$ wherein $R^3$ is selected from phenyl, optionally substituted with 1, 2, or 3 substituents selected from $C_{1-4}$alkyl, halo, $C_{1-4}$alkoxy, —CF$_3$, —OCF$_3$, —OCHF$_2$, and —CN; $C_{1-5}$alkyl; $C_{4-5}$cycloalkyl; and —(CH$_2$)$_m$-A wherein m is 0 or 1 and A is selected from amino, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, and 2,4-dimethylisoxazolyl.

In another specific aspect, X is —C(O)R$^3$ wherein $R^3$ is phenyl, optionally substituted with 1, 2, or 3 substituents selected from $C_{1-4}$alkyl, halo, $C_{1-4}$alkoxy, —CF$_3$, —OCF$_3$, —OCHF$_2$, and —CN.

In another specific aspect, X is —C(O)R$^3$ wherein $R^3$ is $C_{1-5}$alkyl or $C_{4-5}$cycloalkyl.

In another specific aspect, X is —C(O)R$^3$ wherein $R^3$ is —(CH$_2$)$_m$-A wherein m is 0 and A is selected from amino, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, and 2,4-dimethylisoxazolyl.

In another specific aspect, X is —C(O)R$^3$ wherein $R^3$ is phenyl, optionally substituted with 1 or 2 substituents selected from $C_{1-4}$alkyl, halo, and —CF$_3$; furanyl; or thiophenyl.

In yet other specific aspects, X is —C(O)R$^3$ wherein $R^3$ is phenyl optionally substituted with 1 or 2 substituents selected from methyl, chloro, fluoro, and —CF$_3$; or $R^3$ is furan-2-yl or thiophen-2-yl.

In a specific aspect, X is —C(O)NR$^4$R$^5$ wherein $R^4$ is hydrogen or $C_{1-3}$alkyl, and $R^5$ is phenyl optionally substituted with 1, 2, or 3 substituents selected from $C_{1-4}$alkyl, halo, $C_{1-4}$alkoxy, —CF$_3$, —OCF$_3$, and —OCHF$_2$.

In another specific aspect, X is —C(O)NR$^4$R$^5$ wherein $R^4$ is hydrogen.

In another specific aspect, X is —C(O)NR$^4$R$^5$ wherein $R^4$ is hydrogen and $R^5$ is phenyl optionally substituted with 1 or 2 substituents selected from $C_{1-4}$alkyl and halo.

In other specific aspects, X is —C(O)NR$^4$R$^5$ wherein $R^4$ is hydrogen and $R^5$ is phenyl optionally substituted with 1 halo, or with one fluoro or chloro.

In a specific aspect, X is —C(O)C(R$^6$R$^7$)R$^8$ wherein $R^6$ is hydrogen or $C_{1-3}$alkyl and $R^7$ is hydrogen, —OH, or $C_{1-3}$alkyl; or $R^6$ and $R^7$ taken together form oxo or —(CH$_2$)$_2$—; and $R^8$ is phenyl or cyclohexyl, wherein phenyl or cyclohexyl are optionally substituted with 1, 2, or 3 substituents selected from $C_{1-4}$alkyl, halo, $C_{1-4}$alkoxy, —CF$_3$, —OCF$_3$, —OCHF$_2$, and —CN.

In another specific aspect, X is —C(O)C(R$^6$R$^7$)R$^8$ wherein $R^6$ is hydrogen.

In another specific aspect, X is —C(O)C(R$^6$R$^7$)R$^8$ wherein $R^8$ is phenyl optionally substituted with 1, 2, or 3 substituents selected from $C_{1-4}$alkyl, halo, $C_{1-4}$alkoxy, —CF$_3$, —OCF$_3$, —OCHF$_2$, and —CN.

In another specific aspect, X is —C(O)C(R$^6$R$^7$)R$^8$ wherein $R^8$ is cyclohexyl optionally substituted with 1, 2, or 3 substituents selected from $C_{1-4}$alkyl, halo, $C_{1-4}$alkoxy, —CF$_3$, —OCF$_3$, —OCHF$_2$, and —CN.

In yet other specific aspects, X is —C(O)C(R$^6$R$^7$)R$^8$ wherein $R^6$ is hydrogen and $R^7$ is hydrogen, —OH, or methyl; or $R^6$ and $R^7$ taken together form oxo or —(CH$_2$)$_2$—; and $R^8$ is phenyl or cyclohexyl, wherein phenyl or cyclohexyl are optionally substituted with 1 or 2 substituents selected from $C_{1-4}$alkyl and halo; or $R^8$ is phenyl or cyclohexyl, wherein phenyl or cyclohexyl are optionally substituted with 1 or 2 substituents selected from methyl, fluoro, and chloro.

In a specific aspect, X is —C(O)C(HR$^9$)OR$^{10}$ wherein $R^9$ is hydrogen or $C_{1-3}$alkyl, and $R^{10}$ is phenyl optionally substituted with 1, 2, or 3 substituents selected from $C_{1-4}$alkyl, halo, $C_{1-4}$alkoxy, —CF$_3$, —OCF$_3$, and —OCHF$_2$.

In another specific aspect, X is —C(O)C(HR$^9$)OR$^{10}$ wherein $R^9$ is hydrogen or methyl.

In other specific aspects, X is —C(O)C(HR$^9$)OR$^{10}$ wherein $R^9$ is hydrogen or methyl and $R^{10}$ is phenyl optionally substituted with 1 or 2 substituents selected from $C_{1-4}$alkyl and halo, or phenyl optionally substituted with 1 or 2 substituents selected from methyl, fluoro, and chloro.

In a specific aspect, X is —S(O)$_2$R$^{11}$ wherein $R^{11}$ is selected from $C_{1-3}$alkyl, —CH$_2$-phenyl, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, 2,4-dimethylisoxazolyl, and phenyl optionally substituted with 1, 2, or 3 substituents selected from $C_{1-4}$alkyl, halo, $C_{1-4}$alkoxy, —$CF_3$, —$OCF_3$, —$OCHF_2$, and —CN.

In another specific aspect, X is —$S(O)_2R^{11}$ wherein $R^{11}$ is $C_{1-3}$alkyl, 2,4-dimethylisoxazolyl, or phenyl, optionally substituted with 1, 2, or 3 substituents selected from $C_{1-4}$alkyl, halo, $C_{1-4}$alkoxy, —$CF_3$, —$OCF_3$, —$OCHF_2$, and —CN.

In other specific aspects, X is —$S(O)_2R^{11}$ wherein $R^{11}$ is methyl or phenyl optionally substituted with 1 or 2 substituents selected from $C_{1-4}$alkyl and halo; or with 1 or 2 substituents selected from methyl, fluoro, and chloro.

In one aspect, the invention provides a compound of formula (I) wherein
$R^1$ is $C_{3-4}$alkyl; and
X is selected from:
(a) —$C(O)OR^2$ wherein $R^2$ is $C_{1-3}$alkyl or phenyl;
(b) —$C(O)R^3$ wherein $R^3$ is phenyl, optionally substituted with 1 or 2 substituents selected from $C_{1-4}$alkyl, halo, and —$CF_3$; furanyl; or thiophenyl;
(c) —$C(O)NR^4R^5$ wherein $R^4$ is hydrogen and $R^5$ is phenyl optionally substituted with 1 or 2 substituents selected from $C_{1-4}$alkyl and halo;
(d) —$C(O)C(R^6R^7)R^8$ wherein $R^6$ is hydrogen and $R^7$ is hydrogen, —OH, or methyl; or $R^6$ and $R^7$ taken together form oxo or —$(CH_2)_2$—; and $R^8$ is phenyl or cyclohexyl, wherein phenyl or cyclohexyl are optionally substituted with 1 or 2 substituents selected from $C_{1-4}$alkyl and halo;
(e) —$C(O)C(HR^9)OR^{10}$ wherein $R^9$ is hydrogen or methyl and $R^{10}$ is phenyl optionally substituted with 1 or 2 substituents selected from $C_{1-4}$alkyl and halo; and
(f) —$S(O)_2R^{11}$ wherein $R^{11}$ is methyl or phenyl, optionally substituted with 1 or 2 substituents selected from $C_{1-4}$alkyl and halo.

The invention further provides a compound of formula (I) wherein:
$R^1$ is isopropyl or tert-butyl; and
X is selected from:
(a) —$C(O)OR^2$ wherein $R^2$ is methyl or phenyl;
(b) —$C(O)R^3$ wherein $R^3$ is phenyl, optionally substituted with 1 or 2 substituents selected from methyl, chloro, fluoro, and —$CF_3$; furan-2-yl; or thiophen-2-yl; and
(c) —$C(O)NR^4R^5$ wherein $R^4$ is hydrogen and $R^5$ is phenyl optionally substituted with 1 fluoro or chloro.

In still other specific aspects, the invention provides the compounds listed in the Examples and in Tables I to IX below.

The chemical naming convention used herein is illustrated for the compound of Example 1:

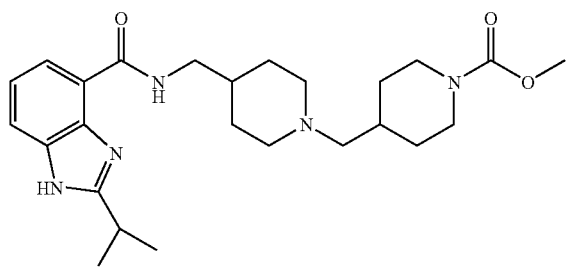

which is designated 4-(4-{[(2-isopropyl-1H-benzoimidazole-4-carbonyl)amino]methyl}-piperidin-1-lmethyl)piperidine-1-carboxylic acid methyl ester, according to the AutoNom software, provided by MDL Information Systems, GmbH (Frankfurt, Germany). The fused ring structure "benzoimidazole" is alternatively named "benzimidazole". The two terms are equivalent as used herein.

As exemplified by particular compounds listed in the tables below, the compounds of the invention may contain a chiral center. Accordingly, the invention includes racemic mixtures, pure stereoisomers, and stereoisomer-enriched mixtures of such isomers, unless otherwise indicated. When a particular stereoisomer is shown, it will be understood by those skilled in the art, that minor amounts of other stereoisomers may be present in the compositions of the invention unless otherwise indicated, provided that any utility of the composition as a whole is not eliminated by the presence of such other isomers.

In one aspect, the invention provides a compound selected from:

4-(4-{[(2-isopropyl-1H-benzoimidazole-4-carbonyl)-amino]methyl}piperidin-1-ylmethyl)piperidine-1-carboxylic acid methyl ester;

4-(4-{[(2-isopropyl-1H-benzoimidazole-4-carbonyl)-amino]-methyl}piperidin-1-ylmethyl)piperidine-1-carboxylic acid phenyl ester;

2-isopropyl-1H-benzoimidazole-4-carboxylic acid {1-[1-(2-chlorobenzoyl)piperidin-4-ylmethyl]piperidin-4-ylmethyl}amide;

2-isopropyl-1H-benzoimidazole-4-carboxylic acid {1-[1-(2,4-difluoro-benzoyl)piperidin-4-ylmethyl]piperidin-4-ylmethyl}amide;

2-isopropyl-1H-benzoimidazole-4-carboxylic acid {1-[1-(furan-2-carbonyl)-piperidin-4-ylmethyl]piperidin-4-ylmethyl}amide;

2-isopropyl-1H-benzoimidazole-4-carboxylic acid {1-[1-(thiophene-2-carbonyl)piperidin-4-ylmethyl]piperidin-4-ylmethyl}amide;

2-isopropyl-1H-benzoimidazole-4-carboxylic acid {1-[1-(2-fluoro-5-trifluoromethylbenzoylpiperidin-4-ylmethyl]piperidin-4-ylmethyl}amide;

2-isopropyl-1H-benzoimidazole-4-carboxylic acid {1-[1-(2-fluoro-phenylcarbamoyl)piperidin-4-ylmethyl]piperidin-4-ylmethyl}-amide;

4-(4-{[(2-tert-butyl-1H-benzoimidazole-4-carbonyl)-amino]-methyl}piperidin-1-ylmethyl)piperidine-1-carboxylic acid methyl ester;

2-tert-butyl-1H-benzoimidazole-4-carboxylic acid {1-[1-(2-fluoro-benzoyl)-piperidin-4-ylmethyl]piperidin-4-ylmethyl}amide;

2-tert-butyl-1H-benzoimidazole-4-carboxylic acid {1-[1-(3-methyl-benzoyl)-piperidin-4-ylmethyl]piperidin-4-ylmethyl}amide; and 2-tert-butyl-1H-benzoimidazole-4-carboxylic acid {1-[1-(4-fluorobenzoyl)-piperidin-4-ylmethyl]piperidin-4-ylmethyl}amide.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl, n-propyl (n-Pr), isopropyl (iPr), n-butyl (n-Bu), sec-butyl, isobutyl, tert-butyl (tBu), n-pentyl, n-hexyl, n-heptyl, n-octyl, n-nonyl, n-decyl and the like.

The term "alkoxy" means a monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl, cycloheptyl, cyclooctyl, and the like.

The term "halo" means fluoro, chloro, bromo or iodo.

The term "oxo" means a double-bonded oxygen atom (=O).

The term "compound" means a compound that was synthetically prepared or produced in any other way, such as by metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;

(b) ameliorating the disease, disorder, or medical condition, i.e., eliminating or causing regression of the disease, disorder, or medical condition in a patient;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), naphthalene-1,5-disulfonic acid and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of formula (I) are prepared by reacting a piperidinylmethyl-piperidinyhnethyl intermediate of formula (II):

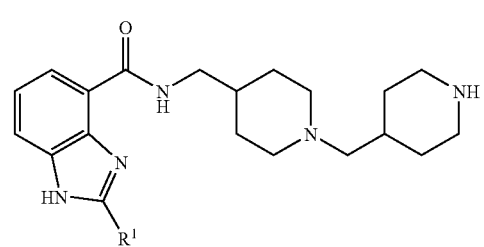

(II)

with a reagent of formula (III):

L-X  (III)

where L is a leaving group, for example a halo, such as chloro, or an acyloxy, sulfonic ester, or oxysuccinimide, and $R^1$ and X are defined as in formula (I).

The reaction is typically conducted by contacting intermediate (II) with between about 1 and about 1.5 equivalents of intermediate (III) in a polar aprotic diluent, such as dichloromethane, in the presence of at least one equivalent of an amine base, such as N,N-diisopropylethylamine. Suitable inert diluents for this process and those described below, also include N,N-dimethylformamide, trichloromethane, 1,1,2,2-tetrachloroethane, tetrahydrofuran, and the like. Suitable amine bases for the processes of the present invention also include triethylamine, pyridine, and the like. The reaction is typically conducted at a temperature in the range of about 0° C. to about 30° C. for about a quarter hour to about 2 hours, or until the reaction is substantially complete. Exemplary reagents L-X in which L is chloro include methyl chloroformate, phenyl chloroformate, chlorobenzoyl chloride, and methanesulfonyl chloride.

In an alternative method of synthesis, compounds of formula (I) in which X is selected from —C(O)R³, —C(O)C(R⁶R⁷)R⁸, and —C(O)C(HR⁹)OR¹⁰ can be prepared by the amide coupling reaction of an intermediate of formula (II) with a carboxylic acid of formula (IV):

(IV)

In formula (IV), X' represents R³, C(R⁶R⁷)R⁸, or C(HR⁹)OR¹⁰, such that —C(O)X' corresponds to X, as set forth above formula (IV). In the amide coupling reaction of intermediate (II), between about 1 and about 1.5 equivalents of the carboxylic acid (IV) are first contacted with between 1 and about 1.5 equivalents of a coupling agent such as O-(7-azabenzotrizol-1-yl)-N,N,N',N'-tetramethyluronium hexafluorophosphate (HATU) in a polar aprotic solvent such as dimethylformamide or those discussed above. The acid mixture is then contacted with intermediate (II) in the presence of between about 2 and about 4 equivalents of an amine base, for example, N,N-diisopropylethylamine. The reaction is typically conducted at a temperature in the range of about 0° C. to about 30° C. for about a quarter hour to about 2 hours, or until the reaction is substantially complete.

Suitable alternative coupling agents include N-ethyl-N'-(3-dimethylaminopropyl)carbodiimide hydrochloride (EDC), 1,1'-carbonyldiimidazole (CDI) 1,3 dicyclohexylcarbodiimide (DCC), and benzotriazol-1-yloxytripyrrolidino-phosphonium hexafluorophosphate (PyBop). The coupling agents may be combined with promoting agents, for example, 1-hydroxy-7-azabenzotriazole (HOAt), hydroxybenzotriazole (HOBt), or 1,4-diazabicyclo[2,2,2]octane (DABCO).

In yet another alternative process, compounds of formula (I) in which X is —C(O)NHR⁵ can be prepared by reacting an intermediate of formula (II) with an isocyanate of the form:

O=C=N—R⁵ (V)

The reaction is typically conducted by contacting intermediate (II) with between about 1 and about 1.5 equivalents of intermediate (V) in a polar aprotic diluent in the presence of at between about 2 and about 4 equivalents of an amine base. The reaction is typically conducted at a temperature in the range of about 0° C. to about 30° C. for about a quarter hour to about 24 hours, or until the reaction is substantially complete.

The product of formula (I) is isolated and purified by conventional procedures. For example, the product can be concentrated to dryness under reduced pressure and the residue purified by HPLC chromatography.

The piperidinylmethyl-piperidinylmethyl intermediates of formula (II) are prepared from readily available starting materials by the procedure illustrated in Scheme A.

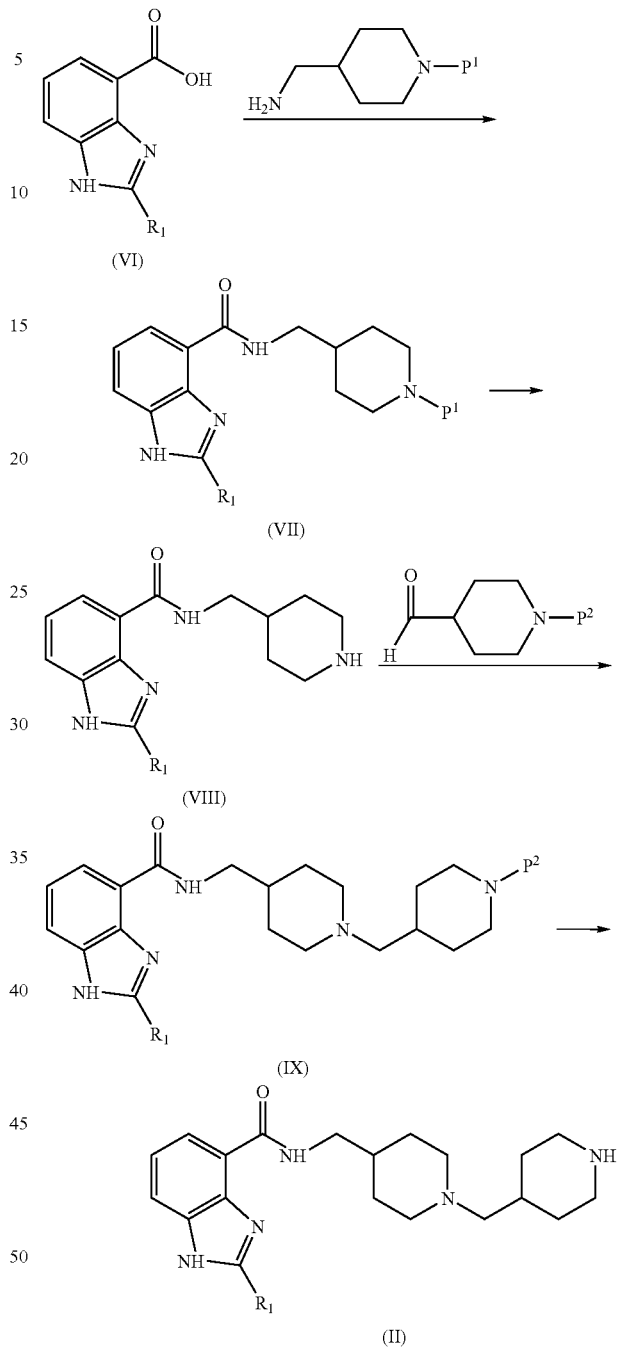

where P¹ and P² independently represent an amino protecting group, such as tert-butoxycarbonyl (Boc).

First, a carboxylic acid of formula (VI) is reacted with a protected aminomethyl piperidine to form a protected intermediate of formula (VII). This reaction is typically conducted by contacting (VI) with between about 1 and about 2 equivalents of protected aminomethylpiperidine in a polar aprotic diluent, in the presence of an amide coupling agent described above, for example N-ethyl-N'-(3-dimethylaminopropyl)carbodiimide hydrochloride (EDC) combined with hydroxybenzotriazole (HOBt) or 1,1'-carbonyldiimidazole (CDI) combined with 1,4-diazabicyclo[2,2,2]octane (DABCO). The reaction is typically conducted at a temperature in the range of about 0° C. to about 60° C. for between about 1 and about 24 hours or until the reaction is substantially complete.

The protecting group $P^1$ is removed from intermediate (VII) by conventional means to provide intermediate (VII). For example, when Boc is used as the protecting group, it may be removed by treatment with an acid, such as trifluoroacetic acid or hydrochloric acid.

An intermediate of formula (IX) is then formed by the reductive amination of intermediate (VIII) with a protected piperidine-carboxaldehyde. This reaction is typically conducted by contacting (VIII) with between about 1 and about 2 equivalents of the protected piperidine-carboxaldehyde in an inert diluent in the presence of between about 1 and about 2 equivalents of a reducing agent. Optionally, about one equivalent of a weak acid, such as acetic acid can be included to accelerate the reaction. The reaction may be conducted at a temperature between about 0° C. and about 30° C., typically between about 20° C. and about 30° C., for about 0.25 to about 2 hours, or until the reaction is substantially complete.

Suitable inert diluents include dichloromethane, trichloromethane, 1,1,2,2-tetrachloroethane, and the like. Typical reducing agents include sodium triacetoxyborohydride, sodium borohydride, and sodium cyanoborohydride. The product (IX) is isolated by standard procedures. When the amine (VII) is supplied as an acid salt, typically between about 1 and about 3 equivalents of an amine base, such as N,N-diisopropylethylamine, is included in the reaction. Finally, the protecting group $P^2$ is removed from intermediate (IX) by conventional procedures to provide the piperidinyl-methyl-piperidinylmethyl intermediate (II).

A carboxylic acid of formula (VI) can be prepared from a diaminobenzoic acid or ester by the process illustrated in Scheme B:

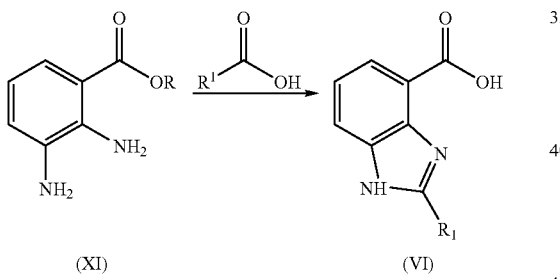

where R represents methyl or hydrogen. Intermediate (XI) is reacted with a carboxylic acid $R^1C(O)OH$ to form the acid intermediate (VI). This reaction is typically conducted by contacting the acid or ester (XI) with between about 2 and about 4 equivalents of the carboxylic acid $R^1C(O)OH$ in an aqueous acidic solution. The reaction is typically conducted at a temperature in the range of about 80° C. to about 100° C. for about 12 to about 72 hours. The pH of the solution is then raised by the addition of base, such as sodium hydroxide, and the product isolated by conventional means.

A convenient process for providing intermediate (XI) as the methyl ester uses 2-amino-3-nitrobenzoic acid methyl ester (X):

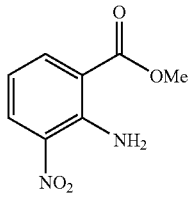

as the starting material. Typically, 2-amino-3-nitrobenzoic acid methyl ester (X) is dissolved in a polar diluent and reduced by exposure to a hydrogen atmosphere in the presence of a transition metal catalyst to provide the diaminobenzoic acid methyl ester (XI). The reaction is typically conducted at ambient temperature for about 12 to about 72 hours.

When the substituent $R^1$ is sterically bulky, as for example, when $R^1$ is tert-butyl, tert-butylbenzimidazole carboxylic acid (VI') can be prepared by the conversion of methyl ester (XI') according to a two-step process, as illustrated, for example, in Scheme C:

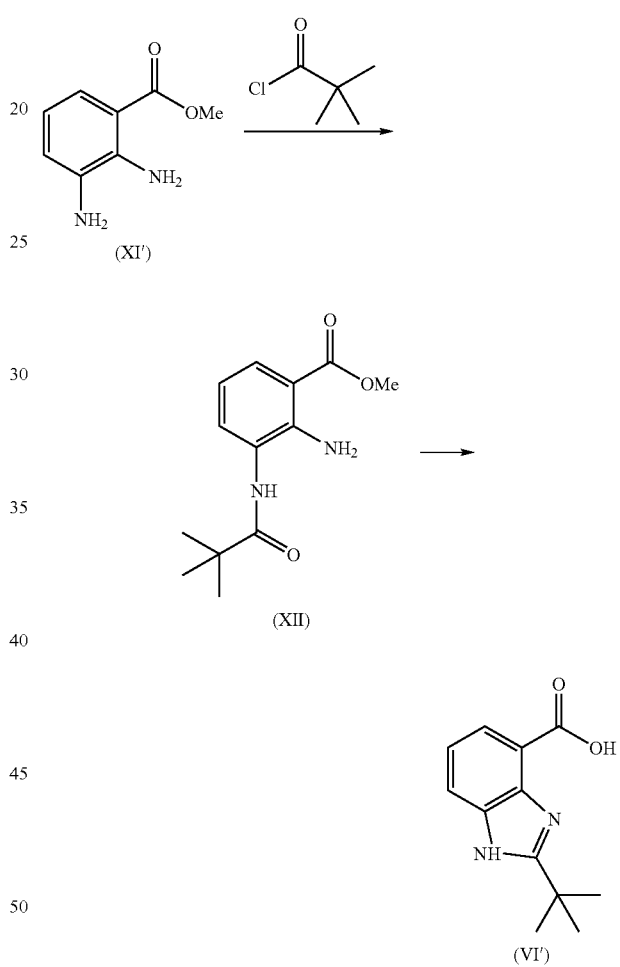

As described in detail in Preparation 3 below, the methyl ester (XI') is first reacted with 2,2-dimethylpropionyl chloride to provide the intermediate (XII) which is refluxed in a strong acid solution, typically, for between about 12 and about 72 hours, to provide the tert-butylbenzimidazole carboxylic acid (VI').

In alternative methods of synthesis, compounds of formula (I) can be prepared according to the process routes illustrated in Scheme D using the reductive amination and other reactions described above, and/or using alternative reactions well known to those skilled in the art.

Scheme D

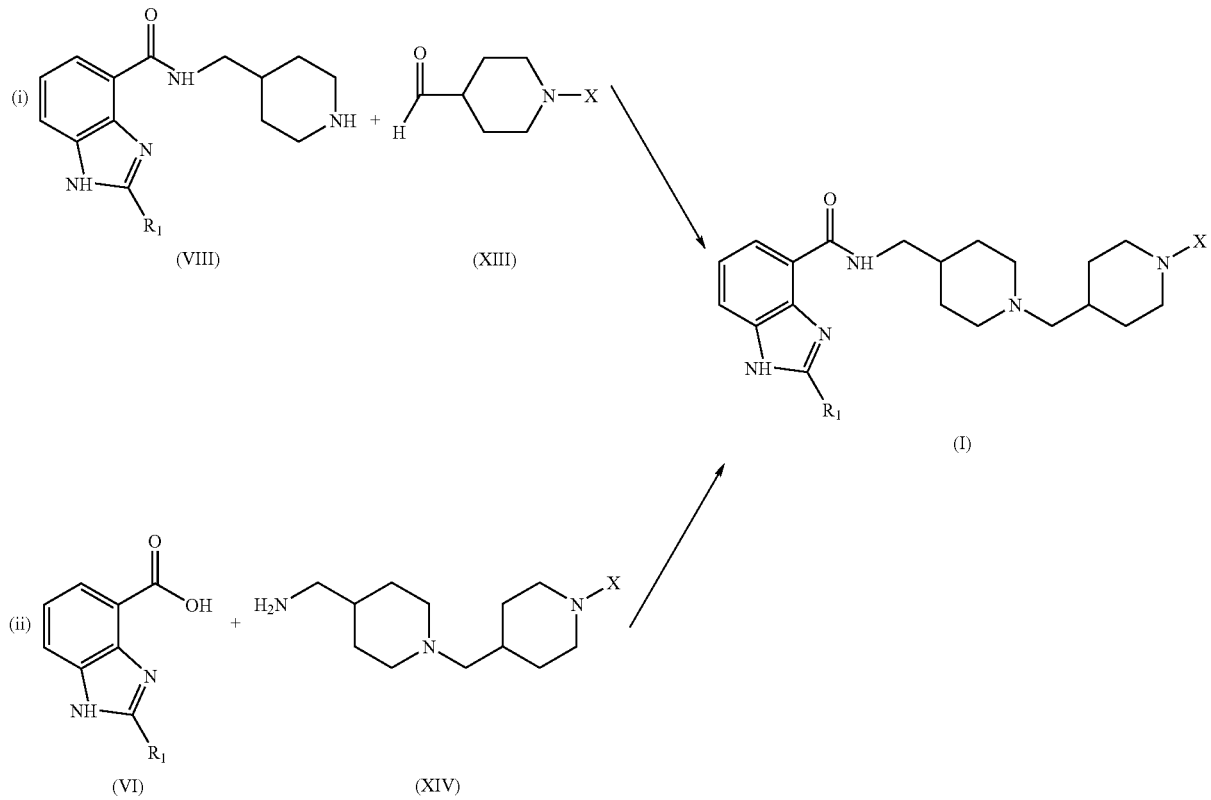

As shown in process route (i), an intermediate of formula (VIII) is reacted with an intermediate of formula (XIII) to provide a compound of formula (I). The reaction is typically performed under the conditions described above for the reaction of amine (VIII) with the protected piperidine-carboxaldehyde in Scheme A.

Intermediate (XI) can be prepared by the reaction of 4-hydroxymethylpiperidine with a reagent L-X, of formula (III), followed by oxidation of the resulting intermediate. For example, for the particular case of X is —C(O)OCH$_3$, intermediate (XIII) can be prepared as shown in Scheme E.

Scheme E

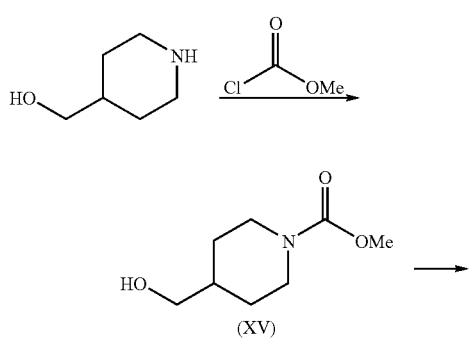

-continued

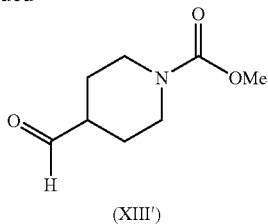

(XIII')

First 4-hydroxymethylpiperidine is reacted with methylchloroformate to form the hydroxymethylpiperidine intermediate (XV). The reaction is typically conducted by contacting 4-hydroxymethylpiperidine in an aqueous solution with between about 3 and about 5 equivalents of methylchloroformate in the presence of between about 3 and about 5 equivalents of base. The reaction is typically conducted at a temperature in the range of about 0° C. to about 30° C. for about 12 to about 72 hours or until the reaction is substantially complete. Intermediate (XV) is then oxidized to form the formylpiperidinyl intermediate (XIII'). The oxidation reaction typically makes use of an oxidation reagent such as a combination of oxalyl chloride and dimethylsulfoxide (Swern oxidation), a chromate reagent, such as pyridinium chlorochromate, or an oxidizing agent, such as sodium hypochlorite, together with a catalyst such as 2,2,6,6-tetramethyl-1-piperidinyloxy free radical (TEMPO).

The preparation of a compound of formula (1) according to process route (i) of Scheme D using intermediate (XIII') is described in Examples 214 and 216 below.

A compound of formula (I) can also be prepared by reacting a carboxylic acid of formula (VI) with an intermediate of formula (XIV), as shown in process route (ii). As illustrated in Scheme F, intermediate (XIV) can be prepared by the reaction of a protected aminomethylpiperidine with intermediate (XIII):

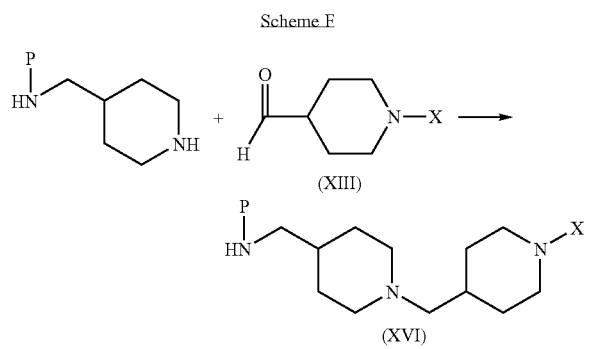

Scheme F where P is an amino-protecting group, to provide a protected intermediate of formula (XVI), followed by a deprotection step. The preparation of compounds according to process route (ii) is described in Preparation 4 and in Examples 14 and 15 below.

The reagents L-X (III), X'C(O)OH (IV), O=C=N—$R^5$ (V) and $R^1$C(O)OH are available commercially or are readily prepared by standard procedures from common starting materials.

Further details regarding specific reaction conditions and other procedures for preparing representative compounds of the invention or intermediates thereto are described in the examples below.

Accordingly, in a method aspect, the invention provides a process for preparing a compound of formula (I), or a salt or stereoisomer thereof, the process comprising (a) reacting a compound of formula (II) with compound of the formula (III); (b) reacting a compound formula (VIII) with a compound of formula (XIII); or (c) reacting a compound of formula (VI) with a compound of formula (XIV) to provide a compound of formula (I), or a salt or stereoisomer thereof.

In an additional method aspect, the invention provides a process for preparing a compound of formula (I) wherein X is selected from —C(O)$R^3$, —C(O)C($R^6R^7$)$R^8$, and —C(O)C(H$R^9$)O$R^{10}$, or a salt or stereoisomer thereof, the process comprising reacting a compound of formula (II) with a compound of formula (IV), wherein X' represents $R^3$, C($R^6R^7$)$R^8$, or C(H$R^9$)O$R^{10}$, to provide a compound of formula (I), or a salt or stereoisomer thereof.

The invention further provides a compound of formula (II), or a salt or stereoisomer or protected derivative thereof, wherein $R^1$ is defined as in formula (I).

Pharmaceutical Compositions

The benzimidazole-carboxamide compounds of the invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt or solvate thereof. Optionally, such pharmaceutical compositions may contain other therapeutic and/or formulating agents if desired.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; including from about 5 to about 70% by weight; and from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in Remington: The Science and Practice of Pharmacy, $20^{th}$ Edition, Lippincott Williams & White, Baltimore, Md. (2000); and H. C. Ansel et al., Pharmaceutical Dosage Forms and Drug Delivery Systems, $7^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention:

FORMULATION EXAMPLE A

Hard gelatin capsules for oral administration are prepared as follows:

| Ingredients | Amount |
|---|---|
| Compound of the invention | 50 mg |
| Lactose (spray-dried) | 200 mg |
| Magnesium stearate | 10 mg |

Representative Procedure: The ingredients are thoroughly blended and then loaded into a hard gelatin capsule (260 mg of composition per capsule).

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are thoroughly blended and then passed through a No. 45 mesh U.S. sieve and loaded into a hard gelatin capsule (200 mg of composition per capsule).

FORMULATION EXAMPLE C

Capsules for oral administration are prepared as follows:

| Ingredients | Amount |
| --- | --- |
| Compound of the invention | 10 mg |
| Polyoxyethylene sorbitan monooleate | 50 mg |
| Starch powder | 250 mg |

Representative Procedure: The ingredients are thoroughly blended and then loaded into a gelatin capsule (310 mg of composition per capsule).

FORMULATION EXAMPLE D

Tablets for oral administration are prepared as follows:

| Ingredients | Amount |
| --- | --- |
| Compound of the invention | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

FORMULATION EXAMPLE E

Tablets for oral administration are prepared as follows:

| Ingredients | Amount |
| --- | --- |
| Compound of the invention | 25 mg |
| Microcrystalline cellulose | 400 mg |
| Silicon dioxide fumed | 10 mg |
| Stearic acid | 5 mg |

Representative Procedure: The ingredients are thoroughly blended and then compressed to form tablets (440 mg of composition per tablet).

FORMULATION EXAMPLE F

Single-scored tablets for oral administration are prepared as follows:

| Ingredients | Amount |
| --- | --- |
| Compound of the invention | 15 mg |
| Cornstarch | 50 mg |
| Croscarmellose sodium | 25 mg |
| Lactose | 120 mg |
| Magnesium stearate | 5 mg |

Representative Procedure: The ingredients are thoroughly blended and compressed to form a single-scored tablet (215 mg of compositions per tablet).

FORMULATION EXAMPLE G

A suspension for oral administration is prepared as follows:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 10 mg of active ingredient per 10 mL of suspension.

FORMULATION EXAMPLE H

A dry powder for administration by inhalation is prepared as follows:

| Ingredients | Amount |
| --- | --- |
| Compound of the invention | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

FORMULATION EXAMPLE I

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of active compound as micronized particles with mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into cartridges with pressurized 1,1,1,2-tetrafluoroethane.

FORMULATION EXAMPLE J

An injectable formulation is prepared as follows:

| Ingredients | Amount |
| --- | --- |
| Compound of the invention | 0.2 g |
| Sodium acetate buffer solution (0.4 M) | 40 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

FORMULATION EXAMPLE K

Capsules for oral administration are prepared as follows:

| Ingredients | Amount |
| --- | --- |
| Compound of the Invention | 4.05 mg |
| Microcrystalline cellulose (Avicel PH 103) | 259.2 mg |
| Magnesium stearate | 0.75 mg |

Representative Procedure: The ingredients are thoroughly blended and then loaded into a gelatin capsule (Size #1, White, Opaque) (264 mg of composition per capsule).

FORMULATION EXAMPLE L

Capsules for oral administration are prepared as follows:

| Ingredients | Amount |
| --- | --- |
| Compound of the Invention | 8.2 mg |
| Microcrystalline cellulose (Avicel PH 103) | 139.05 mg |
| Magnesium stearate | 0.75 mg |

Representative Procedure: The ingredients are thoroughly blended and then loaded into a gelatin capsule (Size #1, White, Opaque) (148 mg of composition per capsule).

It will be understood that any form of the compounds of the invention, (i.e. free base, pharmaceutical salt, or solvate) that is suitable for the particular mode of administration, can be used in the pharmaceutical compositions discussed above.

Utility

The benzimidazole-carboxamide compounds of the invention are 5-$HT_4$ receptor agonists and therefore are expected to be useful for treating medical conditions mediated by 5-$HT_4$ receptors or associated with 5-$HT_4$ receptor activity, i.e. medical conditions which are ameliorated by treatment with a 5-$HT_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-$HT_4$ receptor agonist compounds may be used in the treatment of central nervous system disorders including cognitive disorders, behavioral disorders, mood disorders, and disorders of control of autonomic function.

In particular, the compounds of the invention increase motility of the gastrointestinal (GI) tract and thus are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by 5-$HT_4$ receptors, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by 5-$HT_4$ receptors will range from about 0.0007 to about 20 mg/kg/day of active agent, including from about 0.0007 to about 1 mg/kg/day. For an average 70 kg human, this would amount to from about 0.05 to about 70 mg per day of active agent.

In one aspect of the invention, the compounds of the invention are used to treat chronic constipation. When used to treat chronic constipation, the compounds of the invention will typically be administered orally in a single daily dose or in multiple doses per day. Preferably, the dose for treating chronic constipation will range from about 0.05 to about 70 mg per day.

In another aspect of the invention, the compounds of the invention are used to treat irritable bowel syndrome. When used to treat constipation-predominant irritable bowel syndrome, the compounds of the invention will typically be administered orally in a single daily dose or in multiple doses per day. Preferably, the dose for treating constipation-predominant irritable bowel syndrome will range from about 0.05 to about 70 mg per day.

In another aspect of the invention, the compounds of the invention are used to treat diabetic gastroparesis. When used to treat diabetic gastroparesis, the compounds of the invention will typically be administered orally in a single daily dose or in multiple doses per day. Preferably, the dose for treating diabetic gastroparesis will range from about 0.05 to about 70 mg per day.

In yet another aspect of the invention, the compounds of the invention are used to treat functional dyspepsia. When used to treat functional dyspepsia, the compounds of the invention will typically be administered orally in a single daily dose or in multiple doses per day. Preferably, the dose for treating functional dyspepsia will range from about 0.05 to about 70 mg per day.

The invention also provides a method of treating a mammal having a disease or condition associated with 5-$HT_4$ receptor activity, the method comprising administering to the mammal a therapeutically effective amount of a compound of the invention or of a pharmaceutical composition comprising a compound of the invention.

As described above, compounds of the invention are 5-$HT_4$ receptor agonists. The invention further provides, therefore, a method of agonizing a 5-$HT_4$ receptor in a mammal, the method comprising administering a compound of the invention to the mammal. In addition, the compounds of the invention are also useful as research tools for investigating or studying biological systems or samples having 5-$HT_4$ receptors, or for discovering new 5-$HT_4$ receptor agonists. Moreover, since compounds of the invention exhibit binding selectivity for 5-$HT_4$ receptors as compared with binding to receptors of other 5-HT subtypes, particularly 5-$HT_3$ receptors, such compounds are particularly useful for studying the effects of selective agonism of 5-$HT_4$ receptors in a biological system or sample. Any suitable biological system or sample having 5-$HT_4$ receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like.

In this aspect of the invention, a biological system or sample comprising a 5-$HT_4$ receptor is contacted with a 5-$HT_4$ receptor-agonizing amount of a compound of the invention. The effects of agonizing the 5-$HT_4$ receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of analogs of guanosine triphosphate (GTP), such as [$^{35}$S]GTPγS (guanosine 5'-O-(γ-thio) triphosphate) or GTP-Eu, into isolated membranes via receptor catalyzed exchange of GTP analogs for GDP analogs, ligand-mediated changes in free intracellular calcium ions (measured, for example, with a fluorescence-linked imaging plate reader or FLIPR® from Molecular Devices, Inc.), and measurement of mitogen activated protein kinase (MAPK) activation. A compound of the invention may agonize or increase the activation of 5-$HT_4$ receptors in any of the functional assays listed above, or assays of a similar nature. A 5-$HT_4$ receptor-agonizing amount of a compound of the invention will typically range from about 1 nanomolar to about 500 nanomolar.

Additionally, the compounds of the invention can be used as research tools for discovering new 5-$HT_4$ receptor agonists. In this embodiment, 5-$HT_4$ receptor binding or functional data for a test compound or a group of test compounds is compared to the 5-$HT_4$ receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to be potent agonists of the 5-$HT_4$ receptor and to exhibit substantial selectivity for the 5-$HT_4$ receptor subtype over the 5-$HT_3$ receptor subtype in radioligand binding assays. Further, compounds of the invention of which particular mention was made have demonstrated superior pharmacokinetic properties in a rat model. Such compounds are thus expected to be highly bioavailable upon oral administration. In addition, these compounds have been shown not to exhibit an unacceptable level of inhibition of the potassium ion current in an in vitro voltage-clamp model using isolated whole cells expressing the hERG cardiac potassium channel. The voltage-clamp assay is an accepted pre-clinical method of assessing the potential for pharmaceutical agents to change the pattern of cardiac repolarization, specifically to cause, so-called QT prolongation, which has been associated with cardiac arrhythmia. (Cavero et al., *Opinion on Pharmacotherapy*, 2000, *1*, 947-73, Fermini et al., *Nature Reviews Drug Discovery*, 2003, 2, 439-447) Accordingly, pharmaceutical compositions comprising compounds of the invention are expected to have an acceptable cardiac profile.

There properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

| | |
|---|---|
| Boc = | tert-butoxycarbonyl |
| DMSO = | dimethyl sulfoxide |
| MeCN = | acetonitrile |
| TFA = | trifluoroacetic acid |
| $R_f$ = | retention factor |

Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.

Preparation 1: Synthesis of 2-isopropyl-1H-benzoimidazole-4-carboxylic acid (piperidin-4-ylmethyl)amide a. Preparation of 2,3-diaminobenzoic acid methyl ester To a nitrogen-saturated solution of 2-amino-3-nitrobenzoic acid methyl ester (Chess GmbH, 50 g, 0.26 mol) in absolute ethanol (800 mL) was added palladium hydroxide (Degussa, 20% w/w on carbon, 58.75% w/w water, 10 g). The slurry was degassed then shaken vigorously under hydrogen (4 atm) at room temperature for 48 h. The catalyst was filtered and the filtrate concentrated in vacuo to afford 2,3-diaminobenzoic acid methyl ester as a dark orange oil that solidified on standing (43 g, 0.26 mol, 100%). (m/z): $[M-OCH_3]^+$ calcd for $C_8H_{10}N_2O_2$ 135.05; found 135.3. $^1H$ NMR (300 MHz, DMSO-$d_6$): δ (ppm) 3.74 (s, 3H), 4.80 (br s, 1H), 6.20 (br s, 1H), 6.38 (t, 1H), 6.70 (d, 1H), 7.06 (d, 1H).

b. Preparation of 2-isopropyl-1H-benzoimidazole-4-carboxylic acid

A slurry of 2,3-diaminobenzoic acid methyl ester (21.5 g, 0.13 mol) and isobutyric acid (36.2 mL, 0.39 mol) in aqueous hydrochloric acid (4M, 210 mL) was stirred under reflux for 24 h to afford a homogenous solution. The solution was cooled to 10° C. and the pH raised to 3.5 using aqueous sodium hydroxide solution (4M, approx. 210 mL), while maintaining the temperature below 30° C. The reaction mixture was stirred at room temperature for 2 h, cooled to 10° C., and the resultant precipitate filtered off. The solid cake was transferred to a beaker and acetonitrile (300 mL) was added. The slurry was stirred at room temperature for 1 h then and filtered to afford a grey solid. The solid was dried under vacuum to afford the title intermediate (23 g, 0.11 mol, 87%). (m/z): $[M+H]^+$ calcd for $C_{11}H_{12}N_2O_2$ calcd. 205.09; found 205.3. $^1H$ NMR (300 MHz, DMSO-$d_6$): δ (ppm) 1.27 (d, 6H), 3.39 (m, 1H), 7.29 (t, 1H), 7.78 (m, 2H).

c. Preparation of 4-{[(2-isopropyl-1H-benzoimidazole-4-carbonyl)amino]methyl}-piperidine-1-carboxylic acid tert-butyl ester To a solution of 2-isopropyl-1H-benzoimidazole-4-carboxylic acid (9.0 g, 44.1 mmol) in anhydrous N,N-dimethylformamide (100 mL) was added 4-aminomethyl-piperidine-1-carboxylic acid tert-butyl ester (9.4 g, 44.1 mmol), followed by N,N-diisopropylethylamine (16.9 mL, 97.0 mmol). The solution was stirred for 15 min at room temperature prior to the addition of hydroxybenzotriazole (5.9 g, 44.1 mmol), N-Ethyl-N'-(3-dimethylaminopropyl)carbodiimide hydrochloride (8.4 g, 44.1 mmol), and additional N,N-dimethylformamide (50 mL). The reaction mixture was stirred at room temperature for 16 h, diluted with dichloromethane (300 mL), and washed sequentially with 1M aqueous phosphoric acid, 1M aqueous sodium hydroxide and brine. The solution was then dried over sodium sulfate and concentrated in vacuo to afford a brown oil which solidified upon addition of hexanes. The solid was filtered to give the title intermediate as a beige solid (13.8 g, 36.0 mmol, 78%). (m/z): $[M+H]^+$ calcd for $C_{22}H_{32}N_4O_3$ 401.26; found 401.5; $[M-Boc+H]^+$ 301.5. Retention time (anal. HPLC: 2-90% MeCN/$H_2O$ over 6 min)=3.7 min. $^1H$ NMR (300 MHz, DMSO-$d_6$): δ (ppm) 1.20 (m, 2H), 1.37 (s, 9H), 1.37 (s, 6H), 1.72 (m, 1H), 1.75 (m, 2H), 2.73 (br s, 2H), 3.22 (septet, 1H), 3.36 (m, 2H), 3.95 (m, 2H), 7.26 (t, 1H), 7.63 (d, 1H), 7.79 (d, 1H), 10.11 (t, 1H).

d. Synthesis of 2-isopropyl-1H-benzoimidazole-4-carboxylic acid (piperidin-4-ylmethyl)amide To a solution of 4-{[(2-isopropyl-1H-benzoimidazole-4-carbonyl)amino]methyl}-piperidine-1-carboxylic acid tert-butyl ester (10.8 g, 27.0 mmol) dissolved in dichloromethane (50 mL) at 0° C. was slowly added trifluoroacetic acid (50 mL) in 5 mL portions. The solution was allowed to warm to room temperature, stirred for an additional 20 minutes then evaporated in vacuo. Excess trifluoroacetic acid was removed by co-evaporation with toluene. The residue was then dissolved in a minimal volume of dichloromethane and slowly added to diethyl ether (1 L) at 0° C. The resulting slurry was stirred for 2 h at room temperature then filtered to afford the bis-trifluoroacetate salt of the title compound as a light brown solid (12.7 g, 24.0 mmol, 89%). (m/z): $[M+H]^+$ calcd for $C_{17}H_{24}N_4O$ 301.21; found 301.5. Retention time (anal. HPLC: 2-50% MeCN/$H_2O$ over 6 min)=1.65 min. $^1H$ NMR (300 MHz, MeOD-$d_3$): δ (ppm) 1.59 (d, 6H), 1.60 (m, 1H), 2.03 (m, 2H), 2.04 (m, 1H), 3.00 (m, 2H), 3.43 (m, 2H), 3.45 (m, 2H), 3.63 (septet, 1H), 7.63 (t, 1H), 7.90 (d, 1H), 7.96 (d, 1H), 9.04 (t, 1H).

Preparation 2: Synthesis of 2-isopropyl-1H-benzoimidazole-4-carboxylic acid (1-piperidin-4-ylmethylpiperidin-4-ylmethyl)amide a. Preparation of 4-(4-{[(2-isopropyl-1H-benzoimidazole-4-carbonyl)amino]methyl}-piperidin-1-ylmethyl)piperidine-1-carboxylic acid tert-butyl ester To a suspension of 2-isopropyl-1H-benzoimidazole-4-carboxylic acid (piperidin-4-ylmethyl)amide bis-trifluoroacetate (6.84 g, 12.95 mmol) in dichloromethane (65 mL) at room temperature under nitrogen was added sequentially N,N-diisopropylethylamine (1.67 g, 2.25 mL), a solution of 1-(tert-butoxycarbonyl)piperidine-4-carboxaldehyde (3.16 g, 14.89 mmol) in dichloromethane (5 mL) and sodium triacetoxyborohydride (3.84 g, 18.13 mmol). The resulting mixture was stirred at room temperature for 1.5 h, then acidified to pH 1 with 1M aqueous hydrochloric acid. The aqueous layer was removed, and the organic layer extracted with 1M aqueous hydrochloric acid until no product remained in the organic phase. The combined aqueous layers were washed with dichloromethane, cooled to 0° C. and basified to pH 12 with sodium hydroxide pellets. The solution was then extracted with dichloromethane until no product remained in the aqueous phase, and the combined organic layers washed with brine, dried over sodium sulfate, filtered and concentrated to give the desired product as a brown oil (5.4 g, 10.8 mmol, 84%) which was used without further purification. (m/z): $[M+H]^+$ calcd for $C_{28}H_{43}N_5O_3$ 498.35; found 498.5.

b. Synthesis of 2-isopropyl-1H-benzoimidazole-4-carboxylic acid (1-piperidin-4-ylmethylpiperidin-4-ylmethyl)amide The product of the previous step (5.4 g, 10.8 mmol) was dissolved in dichloromethane (40 mL) and cooled to 0° C. Trifluoroacetic acid (30 mL) was added, and the solution was stirred at 0° C. for a further 0.5 h. The mixture was then concentrated and co-evaporated twice with dichloromethane in vacuo. The resulting residue was dissolved in dichloromethane (20 mL), cooled to 0° C. and basified with 20% w/w aqueous sodium hydroxide (50 mL). The solution was allowed to warm to room temperature over 10 minutes, then filtered. The solid was rinsed with acetonitrile and dried in vacuo to afford a light gray powder (3.09 g, 7.8 mmol, 72%)

which was used without further purification. (m/z): [M+H]+ calcd for $C_{23}H_{35}N_5O$ 398.29; found 398.4.

Preparation 3: Synthesis of 2-tert-butyl-1H-benzoimidazole-4-carboxylic acid (1-piperidin-4-ylmethylpiperidin-4-ylmethyl)amide a. Preparation of 2-amino-3-(2,2-dimethylpropionylamino)benzoic acid methyl ester To a solution of 2,3-diaminobenzoic acid methyl ester (2.3 g, 13.8 mmol) in pyridine (40 mL) at room temperature was added 2,2-dimethylpropionyl chloride (1.7 g, 14.0 mmol). The solution was stirred at for 16 h, evaporated, and the residue partitioned between ethyl acetate (100 mL) and 1M aqueous hydrochloric acid (100 mL). The organic phase was separated, washed with 1M aqueous hydrochloric acid (100 mL), dried over sodium sulfate and evaporated to afford the title compound as a dark oil (2.7 g, 10.8 mmol, 78%) which was used without further purification. (m/z): [M+H]+ calcd for $C_{13}H_{18}N_2O_3$ 251.14; found 250.8 b. Preparation of 2-tert-butyl-1H-benzoimidazole-4-carboxylic acid

A slurry of the product of the previous step (2.7 g, 10.8 mmol) in 4M aqueous hydrochloric acid (100 mL) was stirred under reflux for 24 h to afford a homogenous solution. The solvent was evaporated to afford the hydrochloride salt of the title intermediate as a brick-red solid (2.5 g, 9.8 mmol, 91%). (m/z): [M+H]+ calcd for $C_{12}H_{14}N_2O_2$ 219.12; found 219.3. $^1$H NMR (300 MHz, DMSO-$d_6$): δ (ppm) 1.45 (d, 9H), 3.39 (m, 1H), 7.91 (d, 1H), 7.95 (d, 1H).

c. Preparation of 4-{[(2-tert-butyl-1H-benzoimidazole-4-carbonyl)amino]methyl}-piperidine-1-carboxylic acid tert-butyl ester To a solution of 2-tert-butyl-1H-benzoimidazole-4-carboxylic acid hydrochloride (1.11 g, 4.37 mmol) in anhydrous N,N-dimethylformamide (5 mL) was added 1,1'-carbonyldiimidazole (0.77 g, 4.75 mmol). The solution was stirred at 50° C. for 2 h, then 4-aminomethyl-piperidine-1-carboxylic acid tert-butyl ester (0.94 g, 4.39 mmol) was added, followed by 1,4-diazabicyclo[2,2,2]octane (1.46 g, 13 mmol). The solution was stirred at 50° C. for 16 h, allowed to cool and diluted with water (20 mL) and ethyl acetate (60 mL). The aqueous layer was removed, the organic layer washed with water (20 mL), dried over sodium sulfate and concentrated in vacuo to afford the title intermediate (1.32 g, 3.18 mmol, 73%) which was used without further purification. (m/z): [M+H]+ calcd for $C_{23}H_{34}N_4O_3$ 415.27; found 415.5.

d. Preparation of 2-tert-butyl-1H-benzoimidazole-4-carboxylic acid (piperidin-4-ylmethyl)amide 4-{[(2-tert-Butyl-1H-benzoimidazole-4-carbonyl)amino]methyl}-piperidine-1-carboxylic acid tert-butyl ester (13.5 g, 32.6 mmol) was dissolved in 4N HCl in dioxane (200 mL) and stirred at room temperature for 0.5 h. The resulting solid was filtered to afford the bis hydrochloride salt of the title intermediate (11.3 g, 29.3 mmol, 89%). (m/z): [M+H]+ calcd for $C_{18}H_{26}N_4O$ 315.22; found 315.3. $^1$H NMR (300 MHz, $D_2O$+ MeOD-$d_3$): 1.54 (s, 8H), 1.96 (m, 4H), 2.91 (m, 4H), 3.31 (br s, 1H), 3.45 (d, 2H), 7.56 (t, 1H), 7.89-7.92 (m, 2H)

e. Preparation of 4-(4-{[(2-tert-butyl-1H-benzoimidazole-4-carbonyl)amino]methyl}-piperidin-1-lmethyl)piperidine-1-carboxylic acid tert-butyl ester To a suspension of the bis HCl salt of 2-tert-butyl-1H-benzoimidazole-4-carboxylic acid (piperidin-4-ylmethyl)amide (4.28 g, 11.06 mmol) in dichloromethane (55 mL) at room temperature was added N,N-diisopropylethylamine (1.71 g, 2.31 mL), 1-(tert-butoxycarbonyl)piperidine-4-carboxaldehyde (2.58 g, 12.17 mmol) and sodium triacetoxyborohydride (3.28 g, 15.48 mmol) sequentially. The resulting mixture was stirred at room temperature for 2 h then extracted with 1M aqueous hydrochloric acid. The combined aqueous layers were basified to pH 12 with sodium hydroxide pellets, then extracted with dichloromethane. The combined organic layers were dried over sodium sulfate, filtered and evaporated. The resulting residue was dried under high vacuum to give a light brownish foam (4.9 g, 9.6 mmol, 87%) which was used without further purification. (m/z): [M+H]+ calcd for $C_{29}H_{45}N_5O_3$ 512.35, found: 512.4.

f. Synthesis of 2-tert-butyl-1H-benzoimidazole-4-carboxylic acid (1-piperidin-4-ylmethylpiperidin-4-ylmethyl)amide Crude 4-(4-{[(2-tert-butyl-1H-benzoimidazole-4-carbonyl)amino]methyl}-piperidin-1-ylmethyl)piperidine-1-carboxylic acid tert-butyl ester, prepared as in the previous step (5.1 g, 10 mmol) was treated with a mixture of trifluoroacetic acid (40 mL) and dichloromethane (40 mL) at room temperature for 0.5 h. The mixture was concentrated in vacuo, redissolved in dichloromethane (25 mL) and basified with 1M aqueous sodium hydroxide (15 mL). The organic layer was removed, and the aqueous layer re-extracted with dichloromethane. The combined organic phases were dried over sodium sulfate, filtered, and concentrated in vacuo to afford the desired product as a brown foam (3.6 g, 8.8 mmol, 88%). (m/z): [M+H]+ calcd for $C_{24}H_{37}N_5O$ 412.31, found 412.6.

Preparation 4. Synthesis of 4-(4-aminomethylpiperidin-1-ylmethyl)-piperidine-1-carboxylic acid methyl ester a. Preparation of 4-[4-(tert-butoxycarbonylamino-methyl)piperidin-1y-ylmethyl]-piperidine-1-carboxylic acid methyl ester To a solution of 4-tert-butoxycarbonylaminomethylpiperidine (3.62 g, 16.9 mmol) in dichloromethane (100 mL) was added 4-formylpiperidine-1-carboxylic acid methyl ester (2.89 g, 16.9 mmol) and acetic acid (0.96 mL). The mixture was stirred at room temperature for 10 min prior to the addition of sodium triacetoxyborohydride (5.4 g, 25.5 mmol). The final mixture was stirred at room temperature for 1 h. The reaction was terminated by adding saturated sodium bicarbonate solution (50 mL). The mixture was extracted with dichloromethane (100 mL), and the organic layer was dried over $MgSO_4$. Evaporation of the organic solution afforded a pale yellow oily residue. It was purified by flash silica column chromatography ($CH_2Cl_2$ to 5% MeOH/$CH_2Cl_2$), yielding the title intermediate (4.4 g). (m/z): [M+H]+ calcd for $C_{19}H_{35}N_3O_4$ 370.27; found 370.5.

b. Synthesis of 4-(4-aminomethylpiperidin-1-ylmethyl)-piperidine-1-carboxylic acid methyl ester To a solution of 4-[4-(tert-butoxycarbonylamino-methyl)piperidin-1-ylmethyl]-piperidine-1-carboxylic acid methyl ester (4.4 g, 10.8 mmol) in dichloromethane (20 mL) was added trifluoroacetic acid (20 mL). After stirring for 20 min at room temperature, the solution was evaporated in vacuo, yielding the bis-trifluoroacetate salt of the title compound as a pale yellow oil, which was used without further treatment. (m/z): [M+H]+ calcd for $C_{14}H_{27}N_3O_2$ 270.22; found 270.5.

$^1$H-NMR (CD$_3$OD) δ (ppm) 4.0 (br d, 2H), 3.6 (m, 5H), 2.9-2.7 (m, 6H), 2.1-1.9 (m, 2H), 1.7-1.5 (m, 6H), 1.2-1.0 (m, 4H).

Example 1

Synthesis of 4-(4-{[(2-isopropyl-1H-benzoimidazole-4-carbonyl)-amino]methyl}piperidin-1-ylmethyl)piperidine-1-carboxylic acid methyl ester To a suspension of 2-isopropyl-1H-benzoimidazole-4-carboxylic acid (1-piperidin-4-ylmethylpiperidin-4-ylmethyl) amide (2.9 g, 7.3 mmol) in dichloromethane (50 mL) was added N,N-diisopropylethylamine (1.05 mL, 7.3 mmol). The resulting solution was cooled to 0° C., and methyl chloroformate (576 μL, 7.3 mmol) was added dropwise. The mixture was stirred at 0° C. for 1.5 h, quenched with acetic acid (1 mL) and evaporated in vacuo to afford a beige solid (4.8 g) which was purified via preparative reverse phase HPLC [gradient of 5-10-25% (5-10% over 10 min; 10-25% over 50 min); flow rate 15 mL/min; detection at 280 nm] to afford the bis trifluoroacetate salt of the title compound as a white solid (3.5 g, 5.1 mmol, 70%). (m/z): [M+H]$^+$ calcd for C$_{25}$H$_{37}$N$_5$O$_3$ 456.30; found 456.3. Retention time (anal. HPLC: 2-50% MeCN/H$_2$O over 6 min)=3.06 min.

Example 2

Synthesis of 4-(4-{[(2-isopropyl-1H-benzoimidazole-4-carbonyl)-amino]-methyl}piperidin-1-ylmethyl)piperidine-1-carboxylic acid phenyl ester To a solution of 2-isopropyl-1H-benzoimidazole-4-carboxylic acid (1-piperidin-4-ylmethylpiperidin-4-ylmethyl) amide (0.22 g, 0.55 mmol) and N,N-diisopropylethylamine (0.19 mL) in dichloromethane (5.0 mL) was added phenyl chloroformate (70 μL). The mixture was stirred at room temperature for 10 min, then concentrated in vacuo and purified via preparative reverse phase HPLC to afford the bis trifluoroacetate salt of the title compound as a white solid (98.4 mg, 0.13 mmol, 24%). (m/z): [M+H]$^+$ calcd for C$_{30}$H$_{39}$N$_5$O$_3$ 518.32; found 518.6. $^1$H NMR (300 MHz, MeOD-d$_3$): δ (ppm) 1.14-1.28 (m, 2H), 1.39-1.53 (m, 6H), 1.52-1.62 (m, 2H), 1.70-1.78 (m, 2H), 1.92-2.06 (m, 4H), 2.82-2.97 (m, 6H), 3.32-3.38 (m, 2H), 3.43-3.50 (m, 1H), 3.52-3.69 (m, 2H), 4.04-4.12 (m, 1H), 4.18-4.26 (m, 1H), 6.91-6.98 (m, 1H), 7.08-7.13 (m, 1H), 7.21-7.28 (m, 1H), 7.45-7.50 (m, 1H), 7.73-7.77 (m, 1H), 7.81-7.87 (m, 1H), 9.02-9.32 (brs, 1H).

Example 3

Synthesis of 2-isopropyl-1H-benzoimidazole-4-carboxylic acid {1-[1-(2-chlorobenzoyl) piperidin-4-ylmethyl]piperidin-4-ylmethyl}amide To a suspension of 2-isopropyl-1H-benzoimidazole-4-carboxylic acid (1-piperidin-4-ylmethylpiperidin-4-ylmethyl) amide (2.1 g, 5.29 mmol) in tetrahydrofuran (26 mL) at room temperature was added N,N-diisopropylethylamine (2.05 g, 15.87 mmol), dichloromethane (12 mL) and N,N-dimethylformamide (5 mL). To the resulting suspension was slowly added o-chlorobenzoyl chloride (1.02 g, 5.82 mmol), and the reaction mixture was stirred for 0.5 h at room temperature. The solution was concentrated in vacuo, the resulting residue diluted with acetic acid (7.5 mL) and water (0.5 mL), and the product purified by reverse phase preparative HPLC. The purified salt was partitioned between dichloromethane and 1M aqueous sodium hydroxide, the organic layer removed and the aqueous layer re-extracted with dichloromethane, and the combined organic layers washed with brine, dried over sodium sulfate and concentrated in vacuo to give the title compound as a white foam (1.75 g, 3.26 mmol, 62%). (m/z): [M+H]$^+$ calcd for C$_{30}$H$_{38}$ClN$_5$O$_2$ 536.28; found 536.3. $^1$H NMR (300 MHz, DMSO-d$_6$): 0.90 (br m, 2H), 1.24 (d, 6H), 1.45 (br m, 2H), 1.68 (br m, 8H), 1.96 (m, 1H), 2.72 (br m, 5H), 3.08 (m, 2H), (3.20, m, 3H), 4.40 (br m, 1H), 7.14 (t, 1H), 7.28 (m, 2H), 7.39 (m, 1H), 7.49 (dd, 1H), 7.66 (dd, 1H).

Examples 4-6

Using processes similar to that of Example 3, except replacing the o-chlorobenzoyl chloride with the appropriate chloride reagent, the compounds of Examples 4-6 were prepared.

Example 4 2-isopropyl-1H-benzoimidazole-4-carboxylic acid {1-[1-(2,4-difluoro-benzoyl)piperidin-4-ylmethyl] piperidin-4-ylmethyl}amide; (m/z): [M+H]$^+$ calcd for C$_{30}$H$_{37}$F$_2$N$_5$O$_2$, 538.30; found 538.2. Retention time (anal. HPLC: 2-60% MeCN/H$_2$O over 4 min)=2.12 min. $^1$H NMR (300 MHz, DMSO-d$_6$): 0.92 (m, 2H), 1.30 (m, 2H), 1.38 (d, 6H), 1.53 (m, 2H), 1.60-1.90 (m, 6H), 2.07 (d, 2H), 2.73-2.85 (br m, 3H), 3.05 (t, 1H), 3.22 (septet, 1H), 3.38 (br m, 3H), 4.44 (br d, 1H), 7.10-7.50 (m, 4H), 7.62 (d, 1H), 7.77 (d, 1H), 10.10(br s, 1H).

Example 5 2-isopropyl-1H-benzoimidazole-4-carboxylic acid {1-[1-(furan-2-carbonyl)-piperidin-4-ylmethyl]piperidin-4-ylmethyl}amide; (m/z): [M+H]$^+$ calcd for C$_{28}$H$_{37}$N$_5$O$_3$ 492.30; found 492.2. Retention time (anal. HPLC: 2-65% MeCN/H$_2$O over 4 min)=1.68 min.

Example 6 2-isopropyl-1H-benzoimidazole-4-carboxylic acid {1-[1-(thiophene-2-carbonyl)piperidin-4-ylmethyl] piperidin-4-ylmethyl}amide; (m/z): [M+H]$^+$ calcd for C$_{28}$H$_{37}$N$_5$O$_2$S 508.28; found 508.2. Retention time (anal. HPLC: 2-65% MeCN/H$_2$O over 4 min)=1.94 min.

Example 7

Synthesis of 2-isopropyl-1H-benzoimidazole-4-carboxylic acid {1-[1-(2-fluoro-5-trifluoromethylbenzoylpiperidin-4-ylmethyl]piperidin-4-ylmethyl}amide To a solution of 2-fluoro-5-trifluoromethyl benzoic acid (100 mg, 0.48 mmol) in dimethylformamide (4 mL) at room temperature was added O-(7-azabenzotriazol-1-yl)-N, N,N', N'-tetramethyluronium hexafluorophosphate (200 mg, 0.48 mmol). The mixture was stirred at room temperature for 0.25 h, then 2-isopropyl-1H-benzoimidazole-4-carboxylic acid (1-piperidin-4-ylmethylpiperidin-4-ylmethyl)amide (210 mg, 0.48 mmol) and N,N-diisopropylethylamine (0.184 mL, 0.96 mmol) were added and stirring continued for a further 0.5 h. The solution was evaporated in vacuo and the crude product purified by reverse phase HPLC [gradient of 5-10-25% (5-10% over 10 min; 10-25% over 50 min); flow rate 15 mL/min; detection at 280 nm] to afford the bis trifluoroacetate salt of the title compound as a white solid (70 mg, 0.09 mmol, 18%). (m/z): [M+H]$^+$ calcd for C$_{31}$H$_{37}$F$_4$N$_5$O$_2$ 588.30; found 588.2. Retention time (anal. HPLC: 2-60% MeCN/H$_2$O over 4 min)=2.39 min.

Example 8

Synthesis of 2-isopropyl-1H-benzoimidazole-4-carboxylic acid {1-[1-(2-fluoro-phenylcarbamoyl)piperidin-4-ylmethyl]piperidin-4-ylmethyl}-amide 2-Isopropyl-1H-benzoimidazole-4-carboxylic acid (1-piperidin-4-ylmethylpiperidin-4-ylmethyl)amide (220 mg, 0.55 mmol) was dissolved in N,N-dimethylformamide (2.0 mL) at room temperature. To this solution was added N,N-diisopropylethylamine (143.2 mg, 1.1 mmol) followed by o-fluorophenylisocyanate (75.4 mg, 0.55 mmol). The resulting mixture was stirred at room temperature overnight, concentrated in vacuo and the residue purified by preparative reverse-phase HPLC to afford the bis trifluoroacetate salt of the title compound as a white solid (92.6 mg, 0.12 mmol, 22%). (m/z): [M+H]$^+$ calcd for $C_{30}H_{39}FN_6O_2$ 535.32; found 535.2. Retention time (anal. HPLC: 2-65% MeCN/H$_2$O over 4 min)=2.09 min.

Example 9

Synthesis of 2-isopropyl-1H-benzoimidazole-4-carboxylic acid [1-(1-methanesulfonylpiperidin-4-ylmethyl)piperidin-4-ylmethyl]amide 2-Isopropyl-1H-benzoimidazole-4-carboxylic acid (1-piperidin-4-ylmethylpiperidin-4-ylmethyl)amide (40 mg, 0.1 mmol) was dissolved in N,N-dimethylformamide (1.0 mL) at room temperature. To this solution was added N,N-diisopropylethylamine (0.175 mL, 1 mmol) followed by methanesulfonyl chloride (11.5 mg, 0.1 mmol). The mixture was stirred at room temperature for 16 h, then concentrated in vacuo and the residue purified by preparative reverse-phase HPLC to afford the bis trifluoroacetate salt of the title compound as a white solid (27.2 mg, 0.04 mmol, 40%). (m/z): [M+H]$^+$ calcd for $C_{24}H_{37}N_5O_3S$ 476.27; found 476.2. Retention time (anal. HPLC: 2-65% MeCN/H$_2$O over 4 min)=1.66 min.

Example 10

Synthesis of 4-(4-{[(2-tert-butyl-1H-benzoimidazole-4-carbonyl)-amino]-methyl}piperidin-1-ylmethyl)piperidine-1-carboxylic acid methyl ester To the crude product of Preparation 3 (2.4 g, 5.8 mmol) in dichloromethane (29 mL) at room temperature was added N,N-diisopropylethylamine (1.5 g, 11.6 mmol). The resulting mixture was cooled to 0° C. and methyl chloroformate (660 mg, 6.98 mmol) was added dropwise. The reaction was allowed to warm to room temperature and stirred for a further 10 min. The solution was concentrated, re-dissolved in 50% acetic acid in water, filtered and purified by reversed phase preparative HPLC. The resulting solid was dissolved in dichloromethane and washed with 1M aqueous sodium hydroxide. The aqueous layer was extracted twice with dichloromethane, and the combined organic layers washed with brine, dried over sodium sulfate, filtered and concentrated to give the title compound as a white foam (1.3 g, 2.8 mmol, 48%). (m/z): [M+H]$^+$ calcd for $C_{26}H_{39}N_5O_3$ 470.32, found 470.6. $^1$H NMR (300 MHz, MeOD-d$_3$): δ (ppm) 1.02-1.16 (m, 2H), 1.49 (s, 9H), 1.47-1.7 (m, 4H), 1.82-2.03 (m, 4H), 2.74-2.94 (m, 6H), 3.31-3.40 (m, 2H), 3.54-3.58 (m, 2H), 3.56 (s, 3H), 3.98-4.03 (m, 2H), 7.41-7.46 (m, 1H), 7.71-7.74 (m, 1H), 7.79-7.82 (m, 1H), 9.35 (brs, 1H).

Examples 11-13

Using processes similar to that of Example 10, except replacing the methyl chloroformate with the appropriate chloride reagent, the compounds of Examples 11-13 were prepared.

Example 11 2-tert-butyl-1H-benzoimidazole-4-carboxylic acid {1-[1-(2-fluoro-benzoyl)-piperidin-4-ylmethyl]piperidin-4-ylmethyl}amide; (m/z): [M+H]$^+$ calcd for $C_{31}H_{40}FN_5O_2$ 534.33; found 534.4. Retention time (anal. HPLC: 2-65% MeCN/H$_2$O over 4 min)=2.09 min.

Example 12 2-tert-butyl-1H-benzoimidazole-4-carboxylic acid {1-[1-(3-methyl-benzoyl)-piperidin-4-ylmethyl]piperidin-4-ylmethyl}amide; (m/z): [M+H]$^+$ calcd for $C_{32}H_{43}N_5O_2$ 530.35; found 530.42. Retention time (anal. HPLC: 2-65% MeCN/H$_2$O over 4 min)=2.22.

Example 13 2-tert-butyl-1H-benzoimidazole-4-carboxylic acid {1-[1-(4-fluorobenzoyl)-piperidin-4-ylmethyl]piperidin-4-ylmethyl}amide; (m/z): [M+H]$^+$ calcd for $C_{31}H_{40}FN_5O_2$ 534.33; found 534.4. Retention time (anal. HPLC: 2-65% MeCN/H$_2$O over 4 min)=2.17.

Example 14

Synthesis of 4-[4-({[2-(1-hydroxy-1-methylethyl)-1H-benzoimidazole-4-carbonyl]amino}methyl)piperidin-1-ylmethyl]piperidine-1-carboxylic acid methyl ester Preparation of 2-(1-hydroxy-1-methylethyl)-1H-benzoimidazole-4-carboxylic acid To a solution of 2,3-diaminobenzoic acid methyl ester (1.5 g, 9.2 mmol) in 4 M HCl (50 mL) was added 2-hydroxyisobutyric acid (2.87 g, 27.6 mmol). The mixture was stirred at ~90° C. for 24 h. It was neutralized by use of aqueous sodium hydroxide solution to pH~3, and concentrated to dryness. The residue was suspended in methanol, and filtered through a filter paper. The filtrate was concentrated and the residue was rinsed with ether. The remaining solid residue was dissolved in ethyl acetate, and washed with brine solution. After drying over MgSO$_4$, the organic solution was evaporated in vacuo, yielding the title intermediate as a pale yellow oil (~800 mg). The crude product was used in the next step without further purification. (m/z): [M+H]$^+$ calcd for $C_{11}H_{12}N_2O_3$ 221.09; found 221.1. $^1$H-NMR (CD$_3$OD) δ (ppm) 7.8 (dd, 1H), 7.7 (dd, 1H), 7.2 (m, 1H), 1.3 (s, 6H).

b. Synthesis of 4-[4-({[2-(1-hydroxy-1-methylethyl)-1H-benzoimidazole-4-carbonyl]amino}methyl)piperidin-1-ylmethyl]piperidine-1-carboxylic acid methyl ester To a solution of the benzoimidazole carboxylic acid product of the previous step (0.7 g, 3.18 mmol), the aminomethylpiperidine product of Preparation 4 as the bis-TFA salt (1.2 g, 3.13 mmol), and hydroxybenzotriazole (HOBt) (0.43 g, 3.18 mmol) in dimethylformamide (50 mL) was added triethylamine (1.3 mL, 9.3 mmol) and N-Ethyl-N'-(3-dimethylaminopropyl)carbodiimide hydrochloride (EDC) (0.67 g, 3.5 mmol). The mixture was stirred at room temperature for 12 h, and concentrated to dryness in vacuo. The residue was partitioned between dichloromethane (150 mL) and saturated sodium bicarbonate. The organic layer was dried over MgSO$_4$, and evaporated to dryness, yielding a pale yellow oily residue. It was purified by preparative HPLC to provide the bis-trifluoroacetate salt of the title compound. (m/z):

[M+H]$^+$ calcd for $C_{25}H_{37}N_5O_4$ 472.29; found 472.5. Retention time (anal. HPLC: 5-30% MeCN/H$_2$O over 6 min)=3.67 min. $^1$H-NMR (CD$_3$OD) δ (ppm) 7.9-7.8 (m, 2H), 7.6-7.5 (t, 1H), 4.0 (br d, 2H), 3.6 (s, 5H), 2.9-2.75 (br m, 5H), 2.05-1.9 (br d, 3H), 1.68 (m, 6H), 1.15 (m, 4H).

Example 15

Synthesis of 4-[4-({[2-(2-hydroxy-1-methylethyl)-1H-benzoimidazole-4-carbonyl]amino}methyl)-piperidin-1-ylmethyl]piperidine-1-carboxylic acid methyl ester a. Preparation of 2-(2-hydroxy-1-methylethyl)-1H-benzoimidazole-4-carboxylic acid To a solution of 2,3-diaminobenzoic acid methyl ester (2.1 g, 14.1 mmol) in 4 M HCl (90 mL) was added 2-methyl-3-hydroxypropionic acid methyl ester (5 g, 42.3 mmol). The mixture was stirred at ~90° C. for 24 h. It was neutralized by use of aqueous sodium hydroxide solution to pH~3, and concentrated to dryness. The residue was suspended in methanol, and filtered through a filter paper. After the filtrate was concentrated, the remaining solid residue was dissolved in water and washed with ethyl acetate. The aqueous solution was evaporated in vacuo yielding the title intermediate as a pale yellow oil (~800 mg). The crude product was used in the next step without further purification. (m/z): [M+H]$^+$ calcd for $C_{11}H_{12}N_2O_3$ 221.09; found 221.3. $^1$H-NMR (CD$_3$OD) δ (ppm) 8.1 (d, 1H), 7.9 (m, 1H), 7.6 (t, 1H), 3.8 (m, 2H), 3.6 (m, 1H), 1.4 (d, 3H).

b. Synthesis of 4-[4-({[2-(2-hydroxy-1-methylethyl)-1H-benzoimidazole-4-carbonyl]amino}methyl)piperidin-1-ylmethyl]piperidine-1-carboxylic acid methyl ester To a solution of the benzoimidazole carboxylic acid product of the previous step (0.45 g, 1.75 mmol), the aminomethylpiperidine product of Preparation 4 as the bis-trifluoroacetate salt (0.8 g, 1.6 mmol), and HOBt (0.237 g, 1.75 mmol) in dimethylformamide (50 mL) was added triethylamine (0.98 mL, 7.0 mmol) and EDC (0.353 g, 1.84 mmol). The mixture was stirred at room temperature for 12 h, and concentrated to dryness under reduced pressure. The residue was partitioned between dichloromethane (150 mL) and saturated sodium bicarbonate. The organic layer was dried over MgSO$_4$, and evaporated to dryness, yielding pale yellow oily residue. It was purified by preparative HPLC, yielding the bis-trifluoroacetate salt of the title compound (0.2 g). (m/z): [M+H]$^+$ calcd for $C_{25}H_{37}N_5O_4$ 472.29; found 472.5. Retention time (anal. HPLC: 10-40% MeCN/H$_2$O over 6 min)= 3.31 min. $^1$H-NMR (CD$_3$OD)δ (ppm) 7.9-7.8 (m, 2H), 7.6-7.5 (m, 1H), 4.0 (br d, 2H), 3.85-3.7 (m, 2H), 3.6 (br s, 6H), 3.3 (br, 2H), 2.9-2.6 (br m, 6H), 2.0-1.8 (br, 4H), 1.7-1.5 (m, 6H), 1.4 (m, 3H), 1.1-1.0 (m, 4H).

Additional Compounds of the Invention

Using the procedures of Examples 1-13 and variations thereof, the compounds of Tables I to IX were prepared and characterized by mass spectrometry. In the following tables, blank entries denote hydrogen.

TABLE I

| Example No. | R$^1$ | R$^2$ | Molecular Formula | [M + H]$^+$ calcd | [M + H]$^+$ found |
|---|---|---|---|---|---|
| 16 | iPr | —CH$_2$-phenyl | C$_{31}$H$_{41}$N$_5$O$_3$ | 532.32 | 532.2 |
| 17 | iPr | iPr | C$_{27}$H$_{41}$N$_5$O$_3$ | 484.32 | 484.2 |
| 18 | tBu | phenyl | C$_{31}$H$_{41}$N$_5$O$_3$ | 532.32 | 532.2 |
| 19 | tBu | —CH$_2$-phenyl | C$_{32}$H$_{43}$N$_5$O$_3$ | 546.34 | 546.4 |
| 20 | tBu | iPr | C$_{28}$H$_{43}$N$_5$O$_3$ | 498.34 | 498.4 |

TABLE II

| Example No. | R$^1$ | R$^{3a}$ | R$^{3b}$ | R$^{3c}$ | R$^{3d}$ | R$^{3e}$ | Molecular Formula | [M + H]$^+$ calcd | [M + H]$^+$ found |
|---|---|---|---|---|---|---|---|---|---|
| 21 | tBu | Cl | | | | | C$_{31}$H$_{40}$ClN$_5$O$_2$ | 550.29 | 550.6 |
| 22 | iPr | | | | | | C$_{30}$H$_{39}$N$_5$O$_2$ | 502.31 | 502.4 |
| 23 | iPr | F | | | | | C$_{30}$H$_{38}$FN$_5$O$_2$ | 520.30 | 520.2 |
| 24 | iPr | CH$_3$ | | | | | C$_{31}$H$_{41}$N$_5$O$_2$ | 516.33 | 516.4 |
| 25 | iPr | CF$_3$ | | | | | C$_{31}$H$_{38}$F$_3$N$_5$O$_2$ | 570.30 | 570.2 |
| 26 | iPr | | F | | | | C$_{30}$H$_{38}$F$_{N5}$O$_2$ | 520.30 | 520.2 |
| 27 | iPr | | CH$_3$ | | | | C$_{31}$H$_{41}$N$_5$O$_2$ | 516.33 | 516.4 |
| 28 | iPr | | CF$_3$ | | | | C$_{31}$H$_{38}$F$_3$N$_5$O$_2$ | 570.30 | 570.2 |
| 29 | iPr | | Cl | | | | C$_{30}$H$_{38}$ClN$_5$O$_2$ | 536.27 | 536.2 |
| 30 | iPr | | | CF$_3$ | | | C$_{31}$H$_{38}$F$_3$N$_5$O$_2$ | 570.30 | 570.2 |
| 31 | iPr | | | CH$_3$ | | | C$_{31}$H$_{41}$N$_5$O$_2$ | 516.33 | 516.4 |
| 32 | iPr | | | Cl | | | C$_{30}$H$_{38}$ClN$_5$O$_2$ | 536.27 | 536.2 |
| 33 | iPr | | | OCH$_3$ | | | C$_{31}$H$_{41}$N$_5$O$_3$ | 532.32 | 532.2 |

TABLE II-continued

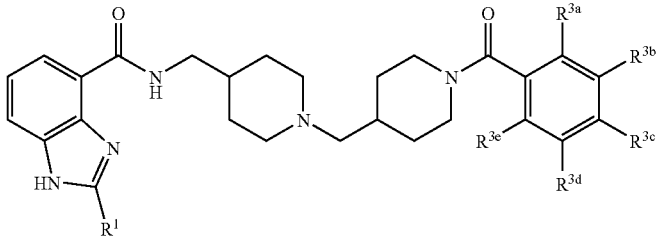

| Example No. | $R^1$ | $R^{3a}$ | $R^{3b}$ | $R^{3c}$ | $R^{3d}$ | $R^{3e}$ | Molecular Formula | $[M + H]^+$ calcd | $[M + H]^+$ found |
|---|---|---|---|---|---|---|---|---|---|
| 34 | iPr | | | F | | | $C_{30}H_{38}FN_5O_2$ | 520.30 | 520.2 |
| 35 | iPr | F | | | | F | $C_{30}H_{37}F_2N_5O_2$ | 538.29 | 538.2 |
| 36 | iPr | F | | | F | | $C_{30}H_{37}F_2N_5O_2$ | 538.29 | 538.2 |
| 37 | iPr | | F | F | | | $C_{30}H_{37}F_2N_5O_2$ | 538.29 | 538.2 |
| 38 | iPr | F | F | | | | $C_{30}H_{37}F_2N_5O_2$ | 538.29 | 538.2 |
| 39 | iPr | | F | | F | | $C_{30}H_{37}F_2N_5O_2$ | 538.29 | 538.2 |
| 40 | iPr | F | | Cl | | | $C_{30}H_{37}ClFN_5O_2$ | 554.26 | 554.4 |
| 41 | iPr | | $CF_3$ | | $CF_3$ | | $C_{32}H_{37}F_6N_5O_2$ | 638.29 | 638.2 |
| 42 | iPr | Cl | | F | | | $C_{30}H_{37}ClFN_5O_2$ | 554.26 | 554.2 |
| 43 | iPr | | Cl | | Cl | | $C_{30}H_{37}Cl_2N_5O_2$ | 570.23 | 570.2 |
| 44 | iPr | | | $OCF_3$ | | | $C_{31}H_{38}F_3N_5O_3$ | 586.29 | 586.2 |
| 45 | iPr | | $CF_3$ | F | | | $C_{31}H_{37}F_4N_5O_2$ | 588.29 | 588.2 |
| 46 | iPr | | Cl | F | | | $C_{30}H_{37}ClFN_5O_2$ | 554.26 | 554.2 |
| 47 | iPr | $OCH_3$ | | Cl | | | $C_{31}H_{40}ClN_5O_3$ | 566.28 | 566.2 |
| 48 | iPr | CN | | | | | $C_{31}H_{38}N_6O_2$ | 527.31 | 527.2 |
| 49 | iPr | Cl | | Cl | | | $C_{30}H_{37}Cl_2N_5O_2$ | 570.23 | 570.2 |
| 50 | iPr | | F | $CF_3$ | | | $C_{31}H_{37}F_4N_5O_2$ | 588.29 | 588.2 |
| 51 | iPr | | CN | | | | $C_{31}H_{38}N_6O_2$ | 527.31 | 527.2 |
| 52 | iPr | | | $OCHF_2$ | | | $C_{31}H_{39}F_2N_5O_3$ | 568.30 | 568.8 |
| 53 | tBu | Cl | | F | | | $C_{31}H_{39}ClFN_5O_2$ | 568.28 | 568.2 |
| 54 | tBu | | Cl | | Cl | | $C_{31}H_{39}Cl_2N_5O_2$ | 584.25 | 584.2 |
| 55 | tBu | | CN | | | | $C_{32}H_{40}N_6O_2$ | 541.32 | 541.4 |
| 56 | tBu | | | $OCF_3$ | | | $C_{32}H_{40}F_3N_5O_3$ | 600.31 | 600.2 |
| 57 | tBu | | $CF_3$ | F | | | $C_{32}H_{39}F_4N_5O_2$ | 602.30 | 602.2 |
| 58 | tBu | | Cl | F | | | $C_{31}H_{39}ClFN_5O_2$ | 568.28 | 568.2 |
| 59 | tBu | $OCH_3$ | | Cl | | | $C_{32}H_{42}ClN_5O_3$ | 580.30 | 580.2 |
| 60 | tBu | CN | | | | | $C_{32}H_{40}N_6O_2$ | 541.32 | 541.4 |
| 61 | tBu | Cl | | Cl | | | $C_{31}H_{39}Cl_2N_5O_2$ | 584.25 | 584.2 |
| 62 | tBu | | F | $CF_3$ | | | $C_{32}H_{39}F_4N_5O_2$ | 602.30 | 602.2 |
| 63 | tBu | F | | | $CF_3$ | | $C_{32}H_{39}F_4N_5O_2$ | 602.30 | 602.4 |
| 64 | tBu | | | CN | | | $C_{32}H_{40}N_6O_2$ | 541.32 | 541.2 |
| 65 | tBu | | | $OCHF_2$ | | | $C_{32}H_{41}F_2N_5O_3$ | 582.32 | 582.4 |
| 66 | tBu | | | | | | $C_{31}H_{41}N_5O_2$ | 516.33 | 516.2 |
| 67 | tBu | $CH_3$ | | | | | $C_{32}H_{43}N_5O_2$ | 530.34 | 530.4 |
| 68 | tBu | $CF_3$ | | | | | $C_{32}H_{40}F_3N_5O_2$ | 584.31 | 584.4 |
| 69 | tBu | | F | | | | $C_{31}H_{40}FN_5O_2$ | 534.32 | 534.2 |
| 70 | tBu | | $CF_3$ | | | | $C_{32}H_{40}F_3N_5O_2$ | 584.31 | 584.4 |
| 71 | tBu | | Cl | | | | $C_{31}H_{40}ClN_5O_2$ | 550.29 | 550.2 |
| 72 | tBu | | | $CF_3$ | | | $C_{32}H_{40}F_3N_5O_2$ | 584.31 | 584.4 |
| 73 | tBu | | | $CH_3$ | | | $C_{32}H_{43}N_5O_2$ | 530.34 | 530.4 |
| 74 | tBu | | | Cl | | | $C_{31}H_{40}ClN_5O_2$ | 550.29 | 550.2 |
| 75 | tBu | | | $OCH_3$ | | | $C_{32}H_{43}N_5O_3$ | 546.34 | 546.4 |
| 76 | tBu | F | | | | F | $C_{31}H_{39}F_2N_5O_2$ | 552.31 | 552.4 |
| 77 | tBu | F | | | F | | $C_{31}H_{39}F_2N_5O_2$ | 552.31 | 552.2 |
| 78 | tBu | | F | F | | | $C_{31}H_{39}F_2N_5O_2$ | 552.31 | 552.2 |
| 79 | tBu | F | F | | | | $C_{31}H_{39}F_2N_5O_2$ | 552.31 | 552.4 |
| 80 | tBu | | F | | F | | $C_{31}H_{39}F_2N_5O_2$ | 552.31 | 552.4 |
| 81 | tBu | F | | F | | | $C_{31}H_{39}F_2N_5O_2$ | 552.31 | 552.2 |
| 82 | tBu | F | | | Cl | | $C_{31}H_{39}ClFN_5O_2$ | 568.28 | 568.2 |
| 83 | tBu | | $CF_3$ | | $CF_3$ | | $C_{33}H_{39}F_6N_5O_2$ | 652.30 | 652.2 |
| 84 | iPr | $OCF_3$ | | | | | $C_{31}H_{38}F_3N_5O_3$ | 586.29 | 586.2 |
| 85 | iPr | | $OCF_3$ | | | | $C_{31}H_{38}F_3N_5O_3$ | 586.29 | 586.2 |
| 86 | tBu | $OCF_3$ | | | | | $C_{32}H_{40}F_3N_5O_3$ | 600.31 | 600.2 |
| 87 | tBu | | $OCF_3$ | | | | $C_{32}H_{40}F_3N_5O_3$ | 600.31 | 600.2 |

TABLE III

| Example No. | R¹ | R³ | Molecular Formula | [M + H]⁺ calcd | [M + H]⁺ found |
|---|---|---|---|---|---|
| 88 | iPr | N(CH₃)₂ | C₂₆H₄₀N₆O₂ | 469.32 | 469.4 |
| 89 | iPr | morpholin-1-yl | C₂₈H₄₂N₆O₃ | 511.33 | 511.4 |
| 90 | iPr | CH₃ | C₂₅H₃₇N₅O₂ | 440.30 | 440.2 |
| 91 | iPr | tetrahydrofuran-2-yl | C₂₈H₄₁N₅O₃ | 496.32 | 496.4 |
| 92 | iPr | —CH₂-thiophen-3-yl | C₂₉H₃₉N₅O₂S | 522.28 | 522.2 |
| 93 | iPr | 2,2-dimethylpropyl | C₂₉H₄₅N₅O₂ | 496.36 | 496.4 |
| 94 | iPr | —CH₂-thiophen-2-yl | C₂₉H₃₉N₅O₂S | 522.28 | 522.2 |
| 95 | iPr | cyclohexyl | C₃₀H₄₅N₅O₂ | 508.36 | 508.4 |
| 96 | iPr | (S)-1-methylpropyl | C₂₈H₄₃N₅O₂ | 482.34 | 482.4 |
| 97 | iPr | —CH₂-naphth-1-yl | C₃₅H₄₃N₅O₂ | 566.34 | 566.4 |
| 98 | iPr | cyclopentyl | C₃₀H₄₅N₅O₂ | 508.36 | 508.4 |
| 99 | iPr | (R)-tetrahydrofuran-2-yl | C₂₈H₄₁N₅O₃ | 496.32 | 496.4 |
| 100 | tBu | furan-2-yl | C₂₉H₃₉N₅O₃ | 506.31 | 506.2 |
| 101 | tBu | —CH₂-thiophen-3-yl | C₃₀H₄₁N₅O₂S | 536.30 | 536.2 |
| 102 | tBu | 2,2-dimethylpropyl | C₃₀H₄₇N₅O₂ | 510.37 | 510.4 |
| 103 | tBu | —CH₂-thiophen-2-yl | C₃₀H₄₁N₅O₂S | 536.30 | 536.2 |
| 104 | tBu | (S)-1-methylpropyl | C₂₉H₄₅N₅O₂ | 496.36 | 496.4 |
| 105 | tBu | —CH₂-naphth-1-yl | C₃₆H₄₅N₅O₂ | 580.36 | 580.4 |
| 106 | tBu | (R)-tetrahydrofuran-2-yl | C₂₉H₄₃N₅O₃ | 510.34 | 510.4 |
| 107 | tBu | (S)-4-oxo-azetidin-2-yl | C₂₈H₄₀N₆O₃ | 509.32 | 510.4 |
| 108 | tBu | pyridin-2-yl | C₃₁H₄₂N₆O₂ | 531.34 | 531.2 |

TABLE IV

| Example No. | R¹ | R⁵ᵃ | R⁵ᵇ | R⁵ᶜ | R⁵ᵈ | R⁵ᵉ | Molecular Formula | [M + H]⁺ calcd | [M + H]⁺ found |
|---|---|---|---|---|---|---|---|---|---|
| 109 | iPr | CH₃ | | | | | C₃₁H₄₂N₆O₂ | 531.34 | 531.4 |
| 110 | iPr | | F | | | | C₃₀H₃₉FN₆O₂ | 535.31 | 535.2 |
| 111 | iPr | | CF₃ | | | | C₃₁H₃₉F₃N₆O₂ | 585.31 | 585.2 |
| 112 | iPr | | OCF₃ | | | | C₃₁H₃₉F₃N₆O₃ | 601.30 | 601.2 |
| 113 | iPr | | | OCHF₂ | | | C₃₁H₄₀F₂N₆O₃ | 583.31 | 583.2 |
| 114 | iPr | | | | | | C₃₀H₄₀N₆O₂ | 517.32 | 517.4 |
| 115 | iPr | CH₃ | | | | CH₃ | C₃₂H₄₄N₆O₂ | 545.35 | 545.4 |
| 116 | iPr | | | OCF₃ | | | C₃₁H₃₉F₃N₆O₃ | 601.30 | 601.2 |
| 117 | iPr | tBu | | | | | C₃₄H₄₈N₆O₂ | 573.38 | 573.4 |
| 118 | iPr | Cl | | | | | C₃₀H₃₉ClN₆O₂ | 551.28 | 551.2 |
| 119 | tBu | Cl | | | | | C₃₁H₄₁ClN₆O₂ | 565.30 | 565.2 |
| 120 | tBu | CH₃ | | | | | C₃₂H₄₄N₆O₂ | 545.35 | 545.5 |
| 121 | tBu | F | | | | | C₃₁H₄₁FN₆O₂ | 549.33 | 549.2 |
| 122 | tBu | CF₃ | | | | | C₃₂H₄₁F₃N₆O₂ | 599.32 | 599.2 |
| 123 | tBu | OCF₃ | | | | | C₃₂H₄₁F₃N₆O₃ | 615.32 | 615.2 |
| 124 | tBu | | | OCHF₂ | | | C₃₂H₄₂F₂N₆O₃ | 597.33 | 597.4 |
| 125 | tBu | | F | | | | C₃₁H₄₁FN₆O₂ | 549.33 | 549.2 |
| 126 | tBu | | | | | | C₃₁H₄₂N₆O₂ | 531.34 | 531.4 |
| 127 | tBu | CH₃ | | | | CH₃ | C₃₃H₄₆N₆O₂ | 559.37 | 559.4 |

TABLE IV-continued

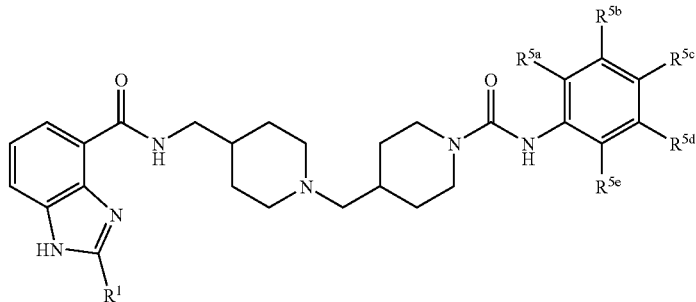

| Example No. | R¹ | R⁵ᵃ | R⁵ᵇ | R⁵ᶜ | R⁵ᵈ | R⁵ᵉ | Molecular Formula | [M + H]⁺ calcd | [M + H]⁺ found |
|---|---|---|---|---|---|---|---|---|---|
| 128 | tBu | | | OCF₃ | | | C₃₂H₄₁F₃N₆O₃ | 615.32 | 615.2 |
| 129 | tBu | tBu | | | | | C₃₅H₅₀N₆O₂ | 587.40 | 587.4 |

TABLE V

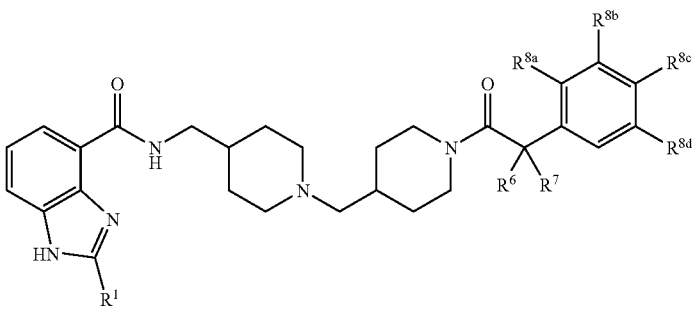

| Example No. | R¹ | R⁶ | R⁷ | R⁸ᵃ | R⁸ᵇ | R⁸ᶜ | R⁸ᵈ | Molecular Formula | [M + H]⁺ calcd | [M + H]⁺ found |
|---|---|---|---|---|---|---|---|---|---|---|
| 130 | iPr | (S)—OH | | | | | | C₃₁H₄₁N₅O₃ | 532.32 | 532.2 |
| 131 | iPr | oxo | | | | | | C₃₁H₃₉N₅O₃ | 530.31 | 530.2 |
| 132 | iPr | | | | | Cl | | C₃₁H₄₀ClN₅O₂ | 550.29 | 550.2 |
| 133 | iPr | (S)—CH₃ | | | | | | C₃₂H₄₃N₅O₂ | 530.34 | 530.4 |
| 134 | iPr | —(CH₂)₂— | | | | | | C₃₃H₄₃N₅O₂ | 542.34 | 542.4 |
| 135 | iPr | | | F | | F | | C₃₁H₃₉F₂N₅O₂ | 552.31 | 552.2 |
| 136 | iPr | | | | F | | | C₃₁H₄₀FN₅O₂ | 534.32 | 534.2 |
| 137 | iPr | | | | Cl | | | C₃₁H₄₀ClN₅O₂ | 550.29 | 551.2 |
| 138 | iPr | | | | F | F | | C₃₁H₃₉F₂N₅O₂ | 552.31 | 552.2 |
| 139 | iPr | | | | F | | F | C₃₁H₃₉F₂N₅O₂ | 552.31 | 553.2 |
| 140 | iPr | | | | | | | C₃₁H₄₁N₅O₂ | 516.33 | 516.4 |
| 141 | tBu | (S)—OH | | | | | | C₃₂H₄₃N₅O₃ | 546.34 | 546.4 |
| 142 | tBu | | | | | F | | C₃₂H₄₂FN₅O₂ | 548.33 | 548.2 |
| 143 | tBu | oxo | | | | | | C₃₂H₄₁N₅O₃ | 544.32 | 544.4 |
| 144 | tBu | | | | | Cl | | C₃₂H₄₂ClN₅O₂ | 564.30 | 565.2 |
| 145 | tBu | CH₃ | | | | 2-methylpropyl | | C₃₇H₅₃N₅O₂ | 600.42 | 600.4 |
| 146 | tBu | (S)—CH₃ | | | | | | C₃₃H₄₅N₅O₂ | 544.36 | 544.4 |
| 147 | tBu | —(CH₂)₂— | | | | | | C₃₄H₄₅N₅O₂ | 556.36 | 556.4 |
| 148 | tBu | | | Cl | | Cl | | C₃₂H₄₁Cl₂N₅O₂ | 598.26 | 599.2 |
| 149 | tBu | | | F | | F | | C₃₂H₄₁F₂N₅O₂ | 566.32 | 566.2 |
| 150 | tBu | | | | F | | | C₃₂H₄₂FN₅O₂ | 548.33 | 548.4 |
| 151 | tBu | | | | | CF₃ | | C₃₃H₄₂F₃N₅O₂ | 598.33 | 598.4 |
| 152 | tBu | | | | CF₃ | | | C₃₃H₄₂F₃N₅O₂ | 598.33 | 598.2 |
| 153 | tBu | | | | Cl | | | C₃₂H₄₂ClN₅O₂ | 564.30 | 564.2 |
| 154 | tBu | | | | F | F | | C₃₂H₄₁F₂N₅O₂ | 566.32 | 566.2 |
| 155 | tBu | | | | F | | F | C₃₂H₄₁F₂N₅O₂ | 566.32 | 566.4 |
| 156 | tBu | | | | | | | C₃₂H₄₃N₅O₂ | 530.34 | 530.4 |

TABLE VI

| Example No. | $R^1$ | $R^7$ | $R^{8a}$ | Molecular Formula | $[M+H]^+$ calcd | $[M+H]^+$ found |
|---|---|---|---|---|---|---|
| 157 | iPr | | (R)-OH | $C_{31}H_{47}N_5O_3$ | 538.37 | 538.4 |
| 158 | iPr | | | $C_{31}H_{47}N_5O_2$ | 522.37 | 522.4 |
| 159 | tBu | | (R)-OH | $C_{32}H_{49}N_5O_3$ | 552.38 | 552.4 |
| 160 | tBu | | | $C_{32}H_{49}N_5O_2$ | 536.39 | 536.4 |

TABLE VII

| Example No. | $R^1$ | $R^9$ | $R^{10a}$ | $R^{10b}$ | Molecular Formula | $[M+H]^+$ calcd | $[M+H]^+$ found |
|---|---|---|---|---|---|---|---|
| 161 | iPr | | | $CH_3$ | $C_{32}H_{43}N_5O_3$ | 546.34 | 546.4 |
| 162 | iPr | | Cl | Cl | $C_{31}H_{39}Cl_2N_5O_3$ | 600.24 | 601.2 |
| 163 | iPr | $CH_3$ | | Cl | $C_{32}H_{42}ClN_5O_3$ | 580.30 | 581.2 |
| 164 | iPr | $CH_3$ | | | $C_{32}H_{43}N_5O_3$ | 546.34 | 546.4 |
| 165 | tBu | | | $CH_3$ | $C_{33}H_{45}N_5O_3$ | 560.35 | 560.4 |
| 166 | tBu | | Cl | Cl | $C_{32}H_{41}Cl_2N_5O_3$ | 614.26 | 615.2 |
| 167 | tBu | $CH_3$ | | Cl | $C_{33}H_{44}ClN_5O_3$ | 594.31 | 595.2 |
| 168 | tBu | $CH_3$ | | | $C_{33}H_{45}N_5O_3$ | 560.35 | 560.4 |

TABLE VIII

| Example No. | $R^1$ | $R^{11}$ | Molecular Formula | $[M+H]^+$ calcd | $[M+H]^+$ found |
|---|---|---|---|---|---|
| 169 | iPr | $CH_3$ | $C_{24}H_{37}N_5O_3S$ | 476.26 | 476.2 |
| 170 | iPr | 2,4-dimethylisoxazol-2yl | $C_{28}H_{40}N_6O_4S$ | 557.28 | 557.2 |
| 171 | iPr | —$CH_2$-phenyl | $C_{30}H_{41}N_5O_3S$ | 552.29 | 552.2 |
| 172 | tBu | 2,4-dimethylisoxazol-2yl | $C_{29}H_{42}N_6O_4S$ | 571.30 | 571.2 |
| 173 | tBu | —$CH_2$-phenyl | $C_{31}H_{43}N_5O_3S$ | 566.31 | 566.2 |

TABLE IX

| Example No. | R¹ | R¹¹ᵃ | R¹¹ᵇ | R¹¹ᶜ | R¹¹ᵈ | Molecular Formula | [M + H]⁺ calcd | [M + H]⁺ found |
|---|---|---|---|---|---|---|---|---|
| 174 | iPr | CF₃ | | | | C₃₀H₃₈F₃N₅O₃S | 606.27 | 606.2 |
| 175 | iPr | CN | | | | C₃₀H₃₈N₆O₃S | 563.27 | 563.2 |
| 176 | iPr | | | OCH₃ | | C₃₀H₄₁N₅O₄S | 568.29 | 568.2 |
| 177 | iPr | | | Cl | | C₂₉H₃₈ClN₅O₃S | 572.24 | 572.2 |
| 178 | iPr | F | | | | C₂₉H₃₈FN₅O₃S | 556.27 | 556.2 |
| 179 | iPr | | | CF₃ | | C₃₀H₃₈F₃N₅O₃S | 606.27 | 606.2 |
| 180 | iPr | | | iPr | | C₃₂H₄₅N₅O₃S | 580.32 | 580.4 |
| 181 | iPr | Cl | | | | C₂₉H₃₈ClN₅O₃S | 572.24 | 572.2 |
| 182 | iPr | CH₃ | | | F | C₃₀H₄₀FN₅O₃S | 570.28 | 570.2 |
| 183 | iPr | Cl | | F | | C₂₉H₃₇ClFN₅O₃S | 590.23 | 590.2 |
| 184 | iPr | CH₃ | Cl | | | C₃₀H₄₀ClN₅O₃S | 586.25 | 586.2 |
| 185 | iPr | | | tBu | | C₃₃H₄₇N₅O₃S | 594.34 | 594.4 |
| 186 | iPr | OCH₃ | | | Cl | C₃₀H₄₀ClN₅O₄S | 602.25 | 602.2 |
| 187 | iPr | | Cl | | | C₂₉H₃₈ClN₅O₃S | 572.24 | 572.2 |
| 188 | iPr | | | | | C₂₉H₃₉N₅O₃S | 538.28 | 538.2 |
| 189 | iPr | | F | | | C₂₉H₃₈FN₅O₃S | 556.27 | 556.2 |
| 190 | iPr | | CH₃ | | | C₃₀H₄₁N₅O₃S | 552.29 | 552.2 |
| 191 | iPr | | | CH₃ | | C₃₀H₄₁N₅O₃S | 552.29 | 552.2 |
| 192 | iPr | CF₃ | | | | C₃₀H₃₈F₃N₅O₃S | 606.27 | 606.2 |
| 193 | iPr | CH₃ | | | | C₃₀H₄₁N₅O₃S | 552.29 | 552.2 |
| 194 | tBu | CN | | | | C₃₁H₄₀N₆O₃S | 577.29 | 577.2 |
| 195 | tBu | | | CF₃ | | C₃₁H₄₀F₃N₅O₃S | 620.28 | 620.2 |
| 196 | tBu | | | iPr | | C₃₃H₄₇N₅O₃S | 594.34 | 594.4 |
| 197 | tBu | Cl | | | | C₃₀H₄₀ClN₅O₃S | 586.25 | 586.2 |
| 198 | tBu | CH₃ | | | F | C₃₁H₄₂FN₅O₃S | 584.30 | 584.2 |
| 199 | tBu | Cl | | F | | C₃₀H₃₉ClFN₅O₃S | 604.24 | 604.2 |
| 200 | tBu | CH₃ | Cl | | | C₃₁H₄₂ClN₅O₃S | 600.27 | 600.2 |
| 201 | tBu | | | tBu | | C₃₄H₄₉N₅O₃S | 608.36 | 608.4 |
| 202 | tBu | OCH₃ | | | Cl | C₃₁H₄₂ClN₅O₄S | 616.26 | 616.2 |
| 203 | tBu | CH₃ | | | | C₃₁H₄₃N₅O₃S | 566.31 | 566.4 |
| 204 | tBu | | CH₃ | | | C₃₁H₄₃N₅O₃S | 566.31 | 566.2 |
| 205 | tBu | | CF₃ | | | C₃₁H₄₀F₃N₅O₃S | 620.28 | 620.2 |
| 206 | tBu | CH₃ | | | | C₃₁H₄₃N₅O₃S | 566.31 | 566.2 |
| 207 | tBu | CF₃ | | | | C₃₁H₄₀F₃N₅O₃S | 620.28 | 620.2 |
| 208 | tBu | | | OCH₃ | | C₃₁H₄₃N₅O₄S | 582.30 | 582.2 |
| 209 | tBu | Cl | | | | C₃₀H₄₀ClN₅O₃S | 586.25 | 586.2 |
| 210 | tBu | F | | | | C₃₀H₄₀FN₅O₃S | 570.28 | 570.2 |
| 211 | tBu | | | Cl | | C₃₀H₄₀ClN₅O₃S | 586.25 | 586.2 |
| 212 | tBu | | | | | C₃₀H₄₁N₅O₃S | 552.29 | 552.2 |
| 213 | tBu | | F | | | C₃₀H₄₀FN₅O₃S | 570.28 | 570.2 |

Example 214

Alternate synthesis of 4-(4-{[(2-isopropyl-1H-benzoimidazole-4-carbonyl)-amino]methyl}piperidin-1-ylmethyl)piperidine-1-carboxylic acid methyl ester a. Preparation of 4-hydroxymethyl-piperidine-1-carboxylic acid methyl ester 4-Hydroxymethylpiperidine (1.0 g, 8.6 mmol) was dissolved in water (15 mL) and cooled to 0° C. To this solution was added dropwise a solution of potassium carbonate (4.8 g, 34.7 mmol) in water (10 mL), followed by methyl chloroformate (2.68 mL, 34.7 mmol). The mixture was stirred vigorously and allowed to warm to room temperature over 2 h. After stirring overnight (16 h), the reaction mixture was acidified with 6M aqueous hydrochloric acid and extracted with dichloromethane (3×60 mL). The extracts were combined, dried over sodium sulfate and filtered. The filtrate was evaporated to yield the title intermediate (1.4 g, 8.1 mmol, 93%) as a colorless oil. (m/z): $C_8H_{15}NO_3$ calcd. 173.11; found 156.2 $[M-H_2O+H]^+$. $^1H$ NMR (300 MHz, DMSO-$d_6$): δ (ppm) 0.98 (m, 2H), 1.52 (m, 1H), 1.63 (br d, 2H), 2.72 (br m, 2H), 3.23 (d, 2H), 3.56 (s; 3H), 3.95 (br d, 2H), 4.48 (br s, 1H).

b. Preparation of 4-formylpiperidine-1-carboxylic acid methyl ester

To a solution of oxalyl chloride (4.1 mL, 8.2 mmol) in dichloromethane (4 mL) at −78° C. was added dropwise a solution of dimethylsulfoxide (1.2 mL, 16.4 mmol) in dichloromethane (4 mL). After stirring for 5 min, a solution of 4-hydroxymethyl-piperidine-1-carboxylic acid methyl ester (1.3 g, 7.5 mmol) in dichloromethane (5 mL) was added. The resulting solution was stirred for another 5 min, then triethylamine (5.2 mL, 37.3 mmol) was added and the mixture allowed to warm to −10° C. After stirring for 1 h, dichloromethane (100 mL) was added, and the organic layer was washed with 1M aqueous phosphoric acid, 1M aqueous sodium hydroxide, and brine. The solution was dried over sodium sulfate then evaporated to afford the title intermediate as a wheat colored oil (1.0 g, 5.8 mmol, 78%). $^1$H NMR (300 MHz, DMSO-$d_6$): δ (ppm) 1.36 (m, 2H), 1.83 (m, 2H), 2.48 (br m, 1H), 2.93 (br t, 2H), 3.56 (s, 3H), 3.80 (br d, 2H), 9.56 (s, 1H).

c. Synthesis of 4-(4-{[(2-isopropyl-1H-benzoimidazole-4-carbonyl)-amino]methyl}piperidin-1-ylmethyl)piperidine--carboxylic acid methyl ester 2-Isopropyl-1H-benzoimidazole-4-carboxylic acid (piperidin-4-ylmethyl)amide, (bis TFA salt; 1.1 g, 2.0 mmol) was suspended in dichloromethane (20 mL) and N,N-di-isopropylethylamine (0.72 mL, 4.0 mmol) was added. When the suspension became a clear solution, acetic acid (0.13 mL, 2.0 mmol) was added, followed by a solution of 4-formylpiperidine-1-carboxylic acid methyl ester (0.54 g, 3.1 mmol) in dichloromethane (20 mL). After stirring for 5 minutes at room temperature, sodium triacetoxyborohydride (0.628 g, 3.1 mmol) was added, and the reaction stirred for an additional 1 h. The aqueous layer was then made alkaline with 1M aqueous sodium hydroxide (35 mL) and extracted with dichloromethane (2×20 mL). The combined organic layers were washed with brine, dried over sodium sulfate and evaporated to yield crude product as a brown solid (1.41 g).

The crude product was purified via preparative HPLC (reverse phase) [gradient of 5-10-25%: 5% MeCN/water (0.1% TFA) to 10% MeCN linear over 10 min; 10% MeCN to 25% MeCN linear over 50 min; flow rate=15 mL/min; detection at 280 nm] to provide the title compound as the bis trifluoroacetate salt, which was then lyophilized. A mixture of 1 M sodium hydroxide and dichloromethane (1:1, 100 mL) was added to the lyophilized bis trifluoroacetate salt. The organic layer was dried over sodium sulfate, filtered, and evaporated, and the resulting solid was lyophilized to provide the title compound as a white solid (0.93 g, 2 mmol, 98% yield, purity 97.5%). (m/z): [M+H]$^+$ calcd for $C_{25}H_{37}N_5O_3$ 456.30; found 456.3. Retention time (anal. HPLC: 2-50% MeCN/H$_2$O over 6 min)=3.06 min. $^1$H NMR (300 MHz, DMSO-$d_6$): 0.92 (m, 2H), 1.30 (m, 2H), 1.38 (d, 6H), 1.53 (m, 1H), 1.60-1.90 (m, 7H), 2.07 (d, 2H), 2.73 (br m, 2H), 2.83 (br d, 2H), 3.22 (septet, 1H), 3.33 (t, 2H), 3.56 (s, 3H), 3.93 (br d, 2H), 7.23 (t, 1H), 7.62 (d, 1H), 7.77 (d, 1H), 10.10 (br s, 1H).

Example 215

Synthesis of crystalline 4-(4{[(2-isopropyl-1H-benzoimidazole-4-carbonyl)-amino]methyl}piperidin-1-ylmethyl)piperidine-1-carboxylic acid methyl ester 4-(4-{[(2-isopropyl-1H-benzoimidazole-4-carbonyl)-amino]methyl}piperidin-1-ylmethyl)piperidine-1-carboxylic acid methyl ester in amorphous solid form, prepared according to the process of Example 214 (300 mg) was dissolved in acetonitrile (15 mL), mixed until complete dissolution, and exposed to the atmosphere resulting in partial evaporation. Crystals were observed to have nucleated within 2 h. Chemical composition of the crystals was confirmed by $^1$H NMR, liquid chromatography/mass spectrometry (LC/MS), and x-ray structure analysis. Crystalline nature of the solid product was confirmed by powder x-ray diffraction, differential scanning calorimetry, and x-ray structure analysis.

Example 216

Synthesis of crystalline 4-(4-{[(2-isopropyl-1H-benzoimidazole-4-carbonyl)-amino]methyl}piperidin-1-ylmethyl)piperidine-1-carboxylic acid methyl ester a. Preparation of 4-hydroxymethyl-piperidine-1-carboxylic acid methyl ester 4-Hydroxymethylpiperidine (47.6 g, 1.0 eq) and water (300 mL) were charged to a flask. The resulting mixture was cooled to 0-10° C. Potassium carbonate (85.7 g, 1.5 eq) dissolved in water (150 mL) and methyl chloroformate (38.4 mL, 1.1 eq) were added while maintaining the temperature at below 10° C. When the addition was complete, the reaction mixture was warmed up to 20-30° C. for 1 hour. After the reaction was complete, dichloromethane (500 mL) was added to the reaction mixture. The organic layer was collected and washed with 1 M phosphoric acid solution (200 mL), saturated sodium bicarbonate solution (200 mL) and saturated sodium chloride solution (200 mL). The organic layer was dried over sodium sulfate (50 g, 1 w/w eq) and then distilled under vacuum to produce the title intermediate. (67.0 g, 90% yield)

b. Preparation of 4-formylpiperidine-1-carboxylic acid methyl ester

4-Hydroxymethylpiperidine-1-carboxylic acid methyl ester (34.7 g, 1.0 eq) was dissolved in dichloromethane and cooled to 0-10° C. A solution of sodium bicarbonate (2.35 g, 0.14 eq) and sodium bromide (2.40 g, 0.10 eq) in water (100 mL) was added over 15 min while maintaining the temperature at 0-10° C. 2,2,6,6-Tetramethyl-1-piperidinyloxy free radical (TEMPO) (0.32 g, 0.01 eq) was added to the mixture, followed by 10-13% w/v sodium hypochlorite solution (135 mL, 1.1 eq) over 1 h with good agitation while maintaining the temperature at 0-10° C. After the reaction was complete, the layers were separated and the organic layer washed with water (150 mL) and dried over sodium sulfate (30 g, 1 w/w eq). The solvent was removed by distillation to provide the title intermediate. (31.0 g, 90% yield)

c. Preparation of 2-isopropyl-1H-benzoimidazole-4-carboxylic acid (piperidin-4-ylmethyl)amide Trifluoroacetic acid (56.0 mL, 10 eq) was added to a flask containing a ~5° C. solution of 4-{[(2-isopropyl-1H-benzoimidazole-4-carbonyl)amino]methyl}-piperidine-1-carboxylic acid tert-butyl ester (30.0 g, 1.0 eq) in dichloromethane (300 mL) while maintaining the temperature below 10° C. The resulting mixture was stirred at 20-30° C. for 2 h. When the reaction was complete, triethylamine (73.2 mL, 7.0 eq) and acetic acid (4.3 mL, 1.0 eq) were added to provide a solution of the title intermediate with an apparent pH of approximately 4 that was used directly in the next step.

d. Synthesis of 4-(4-{[(2-isopropyl-1H-benzoimidazole-4-carbonyl)-amino]methyl}piperidin-1-ylmethyl)piperidine-1-carboxylic acid methyl ester 4-Formylpiperidine-1-carboxylic acid methyl ester (25.7 g, 2.0 eq) was added to the solution prepared in the previous step while maintaining the temperature at 20-30° C. After stirring for 30 min, sodium triacetoxyborohydride (24.3 g, 1.5 eq) was added while maintaining the temperature at 20-30° C. The reaction mixture was stirred at 20-30° C. for 30 min. After the reaction was complete, 1 M hydrochloric acid (300 mL) was added to quench the reaction. The product-containing aqueous layer was collected and washed with dichloromethane (150 mL). The aqueous layer was treated with activated carbon (Darco G60, 6 g, 20% w/w) to remove color. The suspension was stirred for 1 hr, and then filtered through a bed of Celite. Dichloromethane (300 mL) was added to the aqueous solution and the product free-based using 4 N sodium hydroxide by adjusting the pH of the aqueous layer to 12-13. The organic layer was collected and washed with water (300 mL). The organic layer was distilled at 80° C. and solvent exchanged with acetonitrile (2×300 mL), to remove dichloromethane and residual triethylamine. The solids were suspended in acetonitrile (600 mL), and the mixture heated until the solids were dissoved (~75° C.). The solution was cooled until nucleation occured (~55-65° C.) and held for 1 h. The slurry was cooled to 20° C. over 2 h, and then to 0-5° C. over 30 min, followed by stirring at 0-5° C. for 30 min. The solids were filtered and washed with cold acetonitrile (60 mL). The wet cake was dried under vacuum at 60° C. for 6 h to provide the title compound. (28.3 g, 85% yield).

Assay 1: Radioligand Binding Assay on 5-HT$_{4(c)}$ Human Receptors a. Membrane Preparation 5-H$_{4(c)}$ HEK-293 (human embryonic kidney) cells stably-transfected with human 5-HT$_{4(c)}$ receptor cDNA (Bmax=~6.0 pmol/mg protein, as determined using [$^3$H]-GR113808 membrane radioligand binding assay) were grown in T-225 flasks in Dulbecco's Modified Eagles Medium (DMEM) containing 4,500 mg/L D-glucose and pyridoxine hydrochloride (GIBCO-Invitrogen Corp., Carlsbad Calif.: Cat #11965) supplemented with 10% fetal bovine serum (FBS) (GIBCO-Invitrogen Corp.: Cat #10437), 2 mM L-glutamine and (100 units) penicillin-(100 µg) streptomycin/ml (GIBCO-Invitrogen Corp.: Cat #15140) in a 5% CO$_2$, humidified incubator at 37° C. Cells were grown under continuous selection pressure by the addition of 800 µg/mL geneticin (GIBCO-Invitrogen Corp.: Cat #10131) to the medium.

Cells were grown to roughly 60-80% confluency (<35 subculture passages). At 20-22 hours prior to harvesting, cells were washed twice and fed with serum-free DMEM. All steps of the membrane preparation were performed on ice. The cell monolayer was lifted by gentle mechanical agitation and trituration with a 25 mL pipette. Cells were collected by centrifugation at 1000 rpm (5 min).

For the membrane preparation, cell pellets were resuspended in ice-cold 50 mM 4-(2-hydroxyethyl)-1-piperazineethanesulphonic acid (HEPES), pH 7.4 (membrane preparation buffer) (40 mL/total cell yield from 30-40 T225 flasks) and homogenized using a polytron disrupter (setting 19, 2×10 s) on ice. The resultant homogenates were centrifuged at 1200 g for 5 min at 4° C. The pellet was discarded and the supernatant centrifuged at 40,000 g (20 min). The pellet was washed once by resuspension with membrane preparation buffer and centrifugation at 40,000 g (20 min). The final pellet was resuspended in 50 mM HEPES, pH 7.4 (assay buffer) (equivalent 1 T225 flask/1 mL). Protein concentration of the membrane suspension was determined by the method of Bradford (Bradford, 1976). Membranes were stored frozen in aliquots at −80° C.

b. Radioligand Binding Assays

Radioligand binding assays were performed in 1.1 mL 96-deep well polypropylene assay plates (Axygen) in a total assay volume of 400 µL containing 2 µg membrane protein in 50 mM HEPES pH 7.4, containing 0.025% bovine serum albumin (BSA). Saturation binding studies for determination of K$_d$ values of the radioligand were performed using [$^3$H]-GR113808 (Amersham Inc., Bucks, UK: Cat #TRK944; specific activity ~82 Ci/mmol) at 8-12 different concentrations ranging from 0.001 nM-5.0 nM. Displacement assays for determination of pK$_i$ values of compounds were performed with [$^3$H]-GR113808 at 0.15 nM and eleven different concentrations of compound ranging from 10 pM-100 µM.

Test compounds were received as 10 mM stock solutions in DMSO and diluted to 400 µM into 50 mM HEPES pH 7.4 at 25° C., containing 0.1% BSA, and serial dilutions (1:5) then made in the same buffer. Non-specific binding was determined in the presence of 1 µM unlabeled GR113808. Assays were incubated for 60 min at room temperature, and then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 1 µM GR113808. K$_i$ values for test compounds were calculated, in Prism, from the best-fit IC$_{50}$ values, and the K$_d$ value of the radioligand, using the Cheng-Prusoff equation (Cheng and Prusoff, *Biochemical Pharmacology*, 1973, 22, 3099-108): K$_i$=IC$_{50}$/(1+[L]/K$_d$) where [L]=concentration [$^3$H]-GR113808. Results are expressed as the negative decadic logarithm of the K$_i$ values, pK$_i$.

Test compounds having a higher pK$_i$ value in this assay have a higher binding affinity for the 5-HT$_4$ receptor. The compounds of the invention which were tested in this assay had a pK$_i$ value ranging from about 7.0 to about 10.0.

Assay 2: Radioligand Binding Assay on 5-HT$_{3A}$ Human Receptors: Determination of Receptor Subtype Selectivity a. Membrane Preparation 5-HT$_{3A}$ HEK-293 (human embryonic kidney) cells stably-transfected with human 5-HT$_{3A}$ receptor cDNA were obtained from Dr. Michael Bruess (University of Bonn, GDR) (Bmax=~9.0 pmol/mg protein, as determined using [$^3$H]-GR65630 membrane radioligand binding assay). Cells were grown in T-225 flasks or cell factories in 50% Dulbecco's Modified Eagles Medium (DMEM) (GIBCO-Invitrogen Corp., Carlsbad, Calif.: Cat #11965) and 50% Ham's F12 (GIBCO-Invitrogen Corp.: Cat #11765) supplemented with 10% heat inactivated fetal bovine serum (FBS) (Hyclone, Logan, Utah: Cat #SH30070.03) and (50 units) penicillin-(50 µg) streptomycin/ml (GIBCO-Invitrogen Corp.: Cat #15140) in a 5% CO$_2$, humidified incubator at 37° C.

Cells were grown to roughly 70-80% confluency (<35 subculture passages). All steps of the membrane preparation were performed on ice. To harvest the cells, the media was aspirated and cells were rinsed with Ca$^{2+}$, Mg$^{2+}$ free Dulbecco's phosphate buffered saline (dPBS). The cell monolayer was lifted by gentle mechanical agitation. Cells were collected by centrifugation at 1000 rpm (5 min). Subsequent steps of the membrane preparation followed the protocol described above for the membranes expressing 5-HT$_{4(c)}$ receptors.

b. Radioligand Binding Assays

Radioligand binding assays were performed in 96-well polypropylene assay plates in a total assay volume of 200 μL containing 1.5-2 μg membrane protein in 50 mM HEPES pH 7.4, containing 0.025% BSA assay buffer. Saturation binding studies for determination of K$_d$ values of the radioligand were performed using [$^3$H]-GR65630 (PerkinElmer Life Sciences Inc., Boston, Mass.: Cat #NET1011, specific activity ~85 Ci/mmol) at twelve different concentrations ranging from 0.005 nM to 20 nM. Displacement assays for determination of pK$_i$ values of compounds were performed with [$^3$H]-GR65630 at 0.50 nM and eleven different concentrations of compound ranging from 10 pM to 100 μM. Compounds were received as 10 mM stock solutions in DMSO (see section 3.1), diluted to 400 μM into 50 mM HEPES pH 7.4 at 25° C., containing 0.1% BSA, and serial (1:5) dilutions then made in the same buffer. Non-specific binding was determined in the presence of 10 μM unlabeled MDL72222. Assays were incubated for 60 min at room temperature, then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 μL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed using the non-linear regression procedure described above to determine K$_i$ values. The BOTTOM (curve minimum) was fixed to the value for non-specific binding, as determined in the presence of 10 μM MDL72222. The quantity [L] in the Cheng-Prusoff equation was defined as the concentration [$^3$H]-GR65630.

Selectivity for the 5-HT$_4$ receptor subtype with respect to the 5-HT$_3$ receptor subtype was calculated as the ratio K$_i$(5-HT$_{3A}$)/K$_i$(5-HT$_{4(c)}$). The compounds of the invention which were tested in this assay had a 5-HT$_4$/5-HT$_3$ receptor subtype selectivity ranging from about 4000 to upwards of 400,000.

Assay 3

Whole-cell cAMP Accumulation Flashplate Assay with HEK-293 cells expressing human 5-HT$_{4(c)}$ Receptors In this assay, the functional potency of a test compound was determined by measuring the amount of cyclic AMP produced when HEK-293 cells expressing 5-HT$_4$ receptors were contacted with different concentrations of test compound.

a. Cell Culture

HEK-293 (human embryonic kidney) cells stably-transfected with cloned human 5-HT$_{4(c)}$ receptor cDNA were prepared expressing the receptor at two different densities:

(1) at a density of about 0.5-0.6 pmol/mg protein, as determined using a [$^3$H]-GR113808 membrane radioligand binding assay, and (2) at a density of about 6.0 pmol/mg protein. The cells were grown in T-225 flasks in Dulbecco's Modified Eagles Medium (DMEM) containing 4,500 mg/L D-glucose (GIBCO-Invitrogen Corp.: Cat #11965) supplemented with 10% fetal bovine serum (FBS) (GIBCO-Invitrogen Corp.: Cat #10437) and (100 units) penicillin-(100 μg) streptomycin/ml (GIBCO-Invitrogen Corp.: Cat #15140) in a 5% CO$_2$, humidified incubator at 37° C. Cells were grown under continuous selection pressure by the addition of geneticin (800 μg/mL: GIBCO-Invitrogen Corp.: Cat #10131) to the medium.

b. Cell Preparation

Cells were grown to roughly 60-80% confluency. Twenty to twenty-two hours prior to assay, cells were washed twice, and fed, with serum-free DMEM containing 4,500 mg/L D-glucose (GIBCO-Invitrogen Corp.: Cat #11965). To harvest the cells, the media was aspirated and 10 mL Versene (GIBCO-Invitrogen Corp.: Cat #15040) was added to each T-225 flask. Cells were incubated for 5 min at RT and then dislodged from the flask by mechanical agitation. The cell suspension was transferred to a centrifuge tube containing an equal volume of pre-warmed (37° C.) dPBS and centrifuged for 5 min at 1000 rpm. The supernatant was discarded and the pellet was re-suspended in pre-warmed (37° C.) stimulation buffer (10 mL equivalent per 2-3 T-225 flasks). This time was noted and marked as time zero. The cells were counted with a Coulter counter (count above 8 μm, flask yield was 1-2×10$^7$ cells/flask). Cells were resuspended at a concentration of 5×10$^5$ cells/ml in pre-warmed (37° C.) stimulation buffer (as provided in the flashplate kit) and preincubated at 37° C. for 10 min.

cAMP assays were performed in a radioimmunoassay format using the Flashplate Adenylyl Cyclase Activation Assay System with $^{125}$I-cAMP (SMP004B, PerkinElmer Life Sciences Inc., Boston, Mass.), according to the manufacturer's instructions.

Cells were grown and prepared as described above. Final cell concentrations in the assay were 25×10$^3$ cells/well and the final assay volume was 100 μL. Test compounds were received as 10 mM stock solutions in DMSO, diluted to 400 μM into 50 mM HEPES pH 7.4 at 25° C., containing 0.1% BSA, and serial (1:5) dilutions then made in the same buffer. Cyclic AMP accumulation assays were performed with 11 different concentrations of compound ranging from 10 pM to 100 μM (final assay concentrations). A 5-HT concentration-response curve (10 pM to 100 μM) was included on every plate. The cells were incubated, with shaking, at 37° C. for 15 min and the reaction terminated by addition of 100 μl of ice-cold detection buffer (as provided in the flashplate kit) to each well. The plates were sealed and incubated at 4° C. overnight. Bound radioactivity was quantified by scintillation proximity spectroscopy using the Topcount (Packard BioScience Co., Meriden, Conn.).

The amount of cAMP produced per mL of reaction was extrapolated from the cAMP standard curve, according to the instructions provided in the manufacturer's user manual. Data were analyzed by nonlinear regression analysis with the GraphPad Prism Software package using the 3-parameter sigmoidal dose-response model (slope constrained to unity). Potency data are reported as pEC$_{50}$ values, the negative decadic logarithm of the EC$_{50}$ value, where EC$_{50}$ is the effective concentration for a 50% maximal response.

Test compounds exhibiting a higher pEC$_{50}$ value in this assay have a higher potency for agonizing the 5-HT$_4$ receptor. The compounds of the invention which were tested in this assay, for example, in the cell line (1) having a density of about 0.5-0.6 pmol/mg protein, had a pEC$_{50}$ value ranging from about 7.5 to about 9.5.

Assay 4

In vitro Voltage Clamp Assay of Inhibition of Potassium Ion Current in Whole Cells Expressing the hERG Cardiac Potassium Channel CHO-K1 cells stably transfected with hERG cDNA were obtained from Gail Robertson at the University of Wisconsin. Cells were held in cryogenic storage until needed. Cells were expanded and passaged in Dulbecco's Modified Eagles Medium/F12 supplemented with 10% fetal bovine serum and 200 µg/mL geneticin. Cells were seeded onto poly-D-lysine (100 µg/mL) coated glass coverslips, in 35 mm² dishes (containing 2 mL medium) at a density that enabled isolated cells to be selected for whole cell voltage-clamp studies. The dishes were maintained in a humidified, 5% $CO_2$ environment at 37° C.

Extracellular solution was prepared at least every 7 days and stored at 4° C. when not in use. The extracellular solution contained (mM): NaCl (137), KCl (4), $CaCl_2$ (1.8), $MgCl_2$ (1), Glucose (10), 4-(2-hydroxyethyl)-1-piperazineethane-sulphonic acid (HEPES) (10), pH 7.4 with NaOH. The extracellular solution, in the absence or presence of test compound, was contained in reservoirs, from which it flowed into the recording chamber at approximately 0.5 mL/min. The intracellular solution was prepared, aliquoted and stored at −20° C. until the day of use. The intracellular solution contained (mM): KCl (130), $MgCl_2$ (1), ethylene glycol-bis(beta-aminoethyl ether) N,N,N',N'-tetra acetic acid salt (EGTA) (5), MgATP (5), 4-(2-hydroxyethyl)-1-piperazineethanesulphonic acid (HEPES) (10), pH 7.2 with KOH. All experiments were performed at room temperature (20-22° C.).

The coverslips on which the cells were seeded were transferred to a recording chamber and perfused continuously. Gigaohm seals were formed between the cell and the patch electrode. Once a stable patch was achieved, recording commenced in the voltage clamp mode, with the initial holding potential at −80 mV. After a stable whole-cell current was achieved, the cells were exposed to test compound. The standard voltage protocol was: step from the holding potential of −80 mV to +20 mV for 4.8 sec, repolarize to −50 mV for 5 sec and then return to the original holding potential (−80 mV). This voltage protocol was run once every 15 sec (0.067 Hz). Peak current amplitudes during the repolarization phase were determined using pClamp software. Test compounds at a concentration of 3 µM were perfused over the cells for 5 minutes, followed by a 5-minute washout period in the absence of compound. Finally a positive control (cisapride, 20 nM) was added to the perfusate to test the function of the cell. The step from −80 mV to +20 mV activates the hERG channel, resulting in an outward current. The step back to −50 mV results in an outward tail current, as the channel recovers from inactivation and deactivates.

Peak current amplitudes during the repolarization phase were determined using pCLAMP software. The control and test article data were exported to Origin® (OriginLab Corp., Northampton Mass.) where the individual current amplitudes were normalized to the initial current amplitude in the absence of compound. The normalized current means and standard errors for each condition were calculated and plotted versus the time course of the experiment.

Comparisons were made between the observed $K^+$ current inhibitions after the five-minute exposure to either the test article or vehicle control (usually 0.3% DMSO). Statistical comparisons between experimental groups were performed using a two-population, independent t-test (Microcal Origin v. 6.0). Differences were considered significant at $p<0.05$.

The smaller the percentage inhibition of the potassium ion current in this assay, the smaller the potential for test compounds to change the pattern of cardiac repolarization when used as therapeutic agents. For example, the compounds of Examples 1-14 which were tested in this assay at a concentration of 3 µM exhibited an inhibition of the potassium ion current of less than about 30%, including, less than about 20%.

Assay 5

In vitro Model of Oral Bioavailability: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

Caco-2 (colon, adenocarcinoma; human) cells were obtained from ATCC (American Type Culture Collection; Rockville, Md.). For the permeation study, cells were seeded at a density of 63,000 cells/cm² on pre-wetted transwells polycarbonate filters (Costar; Cambridge, Mass.). A cell monolayer was formed after 21 days in culture. Following cell culture in the transwell plate, the membrane containing the cell monolayer was detached from the transwell plate and inserted into the diffusion chamber (Costar; Cambridge, Mass.). The diffusion chamber was inserted into the heating block which was equipped with circulating external, thermostatically regulated 37° C. water for temperature control. The air manifold delivered 95% $O_2$/5% $CO_2$ to each half of a diffusion chamber and created a laminar flow pattern across the cell monolayer, which was effective in reducing the unstirred boundary layer.

The permeation study was performed with test compound concentrations at 100 µM and with $^{14}C$-mannitol to monitor the integrity of the monolayer. All experiments were conducted at 37° C. for 60 min. Samples were taken at 0, 30 and 60 min from both the donor and receiver sides of the chamber. Samples were analyzed by HPLC or liquid scintillation counting for test compound and mannitol concentrations. The permeation coefficient ($K_p$) in cm/sec was calculated.

In this assay, a $K_p$ value greater than about $10 \times 10^{-6}$ cm/sec is considered indicative of favorable bioavailability. Those compounds of the invention which were tested in this assay typically exhibited $K_p$ values of between about $10 \times 10^{-6}$ cm/sec and about $50 \times 10^{-6}$ cm/sec.

Assay 6

Pharmacokinetic Study in the Rat

Aqueous solution formulations of test compounds were prepared in 0.1% lactic acid at a pH of between about 5 and about 6. Male Sprague-Dawley rats (CD strain, Charles River Laboratories, Wilmington, Mass.) were dosed with test compounds via intravenous administration (IV) at a dose of 2.5 mg/kg or by oral gavage (PO) at a dose of 5 mg/kg. The dosing volume was 1 mL/kg for IV and 2 mL/kg for PO administration. Serial blood samples were collected from animals pre-dose, and at 2 (IV only), 5, 15, and 30 min, and at 1, 2, 4, 8, and 24 hours post-dose. Concentrations of test compounds in blood plasma were determined by liquid chromatography-mass spectrometry analysis (LC-MS/MS) (MDS SCIEX, API 4000, Applied Biosystems, Foster City, Calif.) with a lower limit of quantitation of 1 ng/mL.

Standard pharmacokinetic parameters were assessed by non-compartmental analysis (Model 201 for IV and Model 200 for PO) using WinNonlin (Version 4.0.1, Pharsight, Mountain View, Calif.). The maximum in the curve of test compound concentration in blood plasma vs. time is denoted $C_{max}$. The area under the concentration vs. time curve from the time of dosing to the last measurable concentration (AUC (0-t)) was calculated by the linear trapezoidal rule. Oral bioavailability (F(%)), i.e. the dose-normalized ratio of AUC(0-t) for PO administration to AUC(0-t) for IV administration, was calculated as:

$$F(\%)=AUC_{PO}/AUC_{IV} \times Dose_{IV}/Dose_{PO} \times 100\%$$

Test compounds which exhibit larger values of the parameters $C_{max}$, AUC(0-t), and F(%) in this assay are expected to have greater bioavailability when administered orally. Preferred compounds of the invention had $C_{max}$ values typically ranging from about 0.06 to about 0.8 μg/mL and AUC(0-t) values typically ranging from about 0.14 to about 1.2 μg·hr/mL. By way of example, the compound of Example 1 had a $C_{max}$ value of 0.8 μg/mL, an AUC(0-t) value of 1.2 μg·hr/mL and oral bioavailability (F(%)) in the rat model of about 75%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (I):

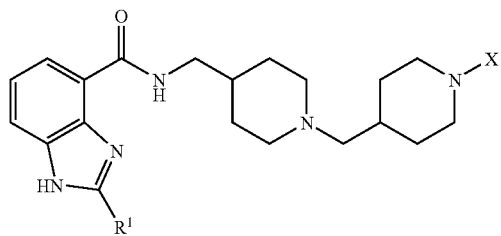

(I)

wherein:
$R^I$ is $C_{3-5}$alkyl, optionally substituted with —OH; and
X is selected from
(a) —C(O)OR² wherein R² is $C_{1-4}$alkyl or —(CH₂)ₙ-phenyl wherein n is 0 or 1;
(b) —C(O)R³ wherein R³ is selected from:
phenyl, optionally substituted with 1, 2, or 3 substituents selected from $C_{1-4}$alkyl, halo, $C_{1-4}$alkoxy, —CF₃, —OCF₃, —OCHF₂, and —CN,
$C_{1-5}$alkyl,
$C_{4-5}$cycloalkyl, and
—(CH₂)ₘ-A wherein m is 0 or 1 and A is selected from amino, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, and 2,4-dimethylisoxazolyl;
(c) —C(O)NR⁴R⁵ wherein R⁴ is hydrogen or $C_{1-3}$alkyl, and R⁵ is phenyl optionally substituted with 1, 2, or 3 substituents selected from $C_{1-4}$alkyl, halo, $C_{1-4}$alkoxy, —CF₃, —OCF₃, and —OCHF₂;
(d) —C(O)C(R⁶R⁷)R⁸ wherein R⁶ is hydrogen or $C_{1-3}$alkyl and R⁷ is hydrogen, —OH, or $C_{1-3}$alkyl; or R⁶ and R⁷ taken together form oxo or —(CH₂)₂—; and R⁸ is phenyl or cyclohexyl, wherein phenyl or cyclohexyl are optionally substituted with 1, 2, or 3 substituents selected from $C_{1-4}$alkyl, halo, $C_{1-4}$alkoxy, —CF₃, —OCF₃, —OCHF₂, and —CN;
(e) —C(O)C(HR⁹)OR¹⁰ wherein R⁹ is hydrogen or $C_{1-3}$alkyl, and R¹⁰ is phenyl optionally substituted with 1, 2, or 3 substituents selected from $C_{1-4}$alkyl, halo, $C_{1-4}$alkoxy, —CF₃, —OCF₃, and —OCHF₂; and
(f) —S(O)₂R¹¹ wherein R¹¹ is selected from $C_{1-3}$alkyl, —CH₂-phenyl, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, 2,4-dimethylisoxazolyl, and phenyl optionally substituted with 1, 2, or 3 substituents selected from $C_{1-4}$alkyl, halo, $C_{1-4}$alkoxy, —CF₃, —OCF₃, —OCHF₂, and —CN;

or a pharmaceutically-acceptable salt or solvate or stereoisomer thereof.

2. The compound of claim 1 wherein R¹ is $C_{3-5}$alkyl.

3. The compound of claim 2 wherein R¹ is isopropyl or tert-butyl.

4. The compound of claim 2 wherein X is —C(O)OR².

5. The compound of claim 4 wherein R² is $C_{1-3}$alkyl or phenyl.

6. The compound of claim 2 wherein X is —C(O)R³.

7. The compound of claim 6 wherein R³ is phenyl, optionally substituted with 1, 2, or 3 substituents selected from $C_{1-4}$alkyl, halo, $C_{1-4}$alkoxy, —CF₃, —OCF₃, and —OCHF₂.

8. The compound of claim 2 wherein X is —C(O)NR⁴R⁵.

9. The compound of claim 2 wherein:
R¹ is $C_{3-4}$alkyl; and
X is selected from:
(a) —C(O)OR² wherein R² is $C_{1-3}$alkyl or phenyl;
(b) —C(O)R³ wherein R³ is phenyl, optionally substituted with 1 or 2 substituents selected from $C_{1-4}$alkyl, halo, and —CF₃; furanyl; or thiophenyl;
(c) —C(O)NR⁴R⁵ wherein R⁴ is hydrogen and R⁵ is phenyl optionally substituted with 1 or 2 substituents selected from $C_{1-4}$alkyl and halo;
(d) —C(O)C(R⁶R⁷)R⁸ wherein R⁶ is hydrogen and R⁷ is hydrogen, —OH, or methyl; or R⁶ and R⁷ taken together form oxo or —(CH₂)₂—; and R⁸ is phenyl or cyclohexyl, wherein phenyl or cyclohexyl are optionally substituted with 1 or 2 substituents selected from $C_{1-4}$alkyl and halo;
(e) —C(O)C(HR⁹)OR¹⁰ wherein R⁹ is hydrogen or methyl and R¹⁰ is phenyl optionally substituted with 1 or 2 substituents selected from $C_{1-4}$alkyl and halo; and
(f) —S(O)₂R¹¹ wherein R¹¹ is methyl or phenyl, optionally substituted with 1 or 2 substituents selected from $C_{1-4}$alkyl and halo.

10. The compound of claim 9 wherein:
R¹ is isopropyl or tert-butyl; and

X is selected from:
- (a) —C(O)OR² wherein R² is methyl or phenyl;
- (b) —C(O)R³ wherein R³ is phenyl, optionally substituted with 1 or 2 substituents selected from methyl, chloro, fluoro, and —CF₃; furan-2-yl; or thiophen-2-yl; and
- (c) —C(O)NR⁴R⁵ wherein R⁴ is hydrogen and R⁵ is phenyl optionally substituted with 1 fluoro or chloro.

11. The compound of claim 2 wherein the compound is selected from:
4-(4-{[(2-isopropyl-1H-benzoimidazole-4-carbonyl)-amino]methyl}piperidin-1-ylmethyl)piperidine-1-carboxylic acid methyl ester;
4-(4-{[(2-isopropyl-1H-benzoimidazole-4-carbonyl)-amino]-methyl}piperidin-1-ylmethyl)piperidine-1-carboxylic acid phenyl ester;
2-isopropyl-1H-benzoimidazole-4-carboxylic acid {1-[1-(2-chlorobenzoyl) piperidin-4-ylmethyl]piperidin-4-ylmethyl}amide;
2-isopropyl-1H-benzoimidazole-4-carboxylic acid {1-[1-(2,4-difluoro-benzoyl) piperidin-4-ylmethyl]piperidin-4-ylmethyl}amide;
2-isopropyl-1H-benzoimidazole-4-carboxylic acid {1-[1-(furan-2-carbonyl)-piperidin-4-ylmethyl]piperidin-4-ylmethyl}amide;
2-isopropyl-1H-benzoimidazole-4-carboxylic acid {1-[1-(thiophene-2-carbonyl)piperidin-4-ylmethyl]piperidin-4-ylmethyl}amide;
2-isopropyl-1H-benzoimidazole-4-carboxylic acid {1-[1-(2-fluoro-5-trifluoromethylbenzoylpiperidin-4-ylmethyl]piperidin-4-ylmethyl}amide;
2-isopropyl-1H-benzoimidazole-4-carboxylic acid {1-[1-(2-fluoro phenylcarbomoyl)piperidin-4-ylmethyl]piperidin-4-ylmethyl}-amide;
4-(4-{[(2-tert-butyl-1H-benzoimidazole-4-carbonyl)-amino]-methyl}piperidin-1-ylmethyl)piperidine-1-carboxylic acid methyl ester;
2-tert-butyl-1H-benzoimidazole-4-carboxylic acid {1-[1-(2-fluoro-benzoyl)-piperidin-4-ylmethyl]piperidin-4-ylmethyl}amide;
2-tert-butyl-1H-benzoimidazole-4-carboxylic acid {1-[1-(3-methyl-benzoyl)-piperidin-4-ylmethyl]piperidin-4-ylmethyl}amide;
2-tert-butyl-1H-benzoimidazole-4-carboxylic acid {1-[1-(4-fluorobenzoyl)-piperidin-4-ylmethyl]piperidin-4-ylmethyl}amide; and
pharmaceutically-acceptable salts and solvates and stereoisomers thereof.

12. A compound selected from:
4-(4-{[(2-isopropyl-1H-benzoimidazole-4-carbonyl)-amino]methyl}piperidin-1-ylmethyl)piperidine-1-carboxylic acid methyl ester;
4-(4-{[(2-tert-butyl-1H-benzoimidazole-4-carbonyl)-amino]-methyl}piperidin-1-ylmethyl)piperidine-1-carboxylic acid methyl ester;
2-tert-butyl-1H-benzoimidazole-4-carboxylic acid {1-[1-(2-fluoro-benzoyl)-piperidin-4-ylmethyl]piperidin-4-ylmethyl}amide; and
pharmaceutically-acceptable salts and solvates and stereoisomers thereof.

13. A pharmaceutical composition comprising a therapeutically effective amount of the compound of claim 1 or claim 12 and a pharmaceutically acceptable carrier.

14. A process for preparing a compound of formula (I),

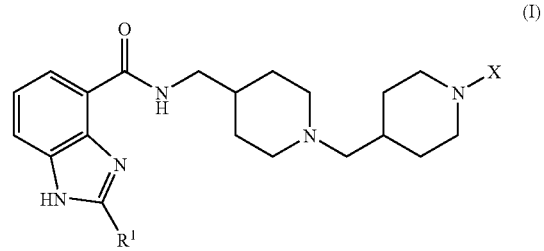

wherein:
R¹ is C₃₋₅alkyl, optionally substituted with —OH; and
X is selected from
- (a) —C(O)OR² wherein R² is C₁₋₄alkyl or —(CH₂)ₙ-phenyl wherein n is 0 or 1;
- (b) —C(O)R³ wherein R³ is selected from:
  phenyl, optionally substituted with 1, 2, or 3 substituents selected from C₁₋₄alkyl, halo, C₁₋₄alkoxy, —CF₃, —OCF₃, and —OCHF₂,
  C₁₋₅alkyl,
  C₄₋₅cycloalkyl, and
  —(CH₂)ₘ-A wherein m is 0 or 1 and A is selected from furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, and 2,4-dimethylisoxazolyl;
- (c) —C(O)NR⁴R⁵ wherein R⁴ is hydrogen or C₁₋₃alkyl, and R⁵ is phenyl optionally substituted with 1, 2, or 3 substituents selected from C₁₋₄alkyl, halo, C₁₋₄alkoxy, —CF₃, —OCF₃, and —OCHF₂;
- (d) —C(O)C(R⁶R⁷)R⁸ wherein R⁶ is hydrogen or C₁₋₃alkyl and R⁷ is hydrogen, —OH, C₁₋₃alkyl, or oxo; or R⁶ and R⁷ form —(CH₂)₂—; and R⁸ is phenyl or cyclohexyl, wherein phenyl or cyclohexyl are optionally substituted with 1, 2, or 3 substituents selected from C₁₋₄alkyl, halo, C₁₋₄alkoxy, —CF₃, —OCF₃, —OCHF₂, and —CN;
- (e) —C(O)C(HR⁹)OR¹⁰ wherein R⁹ is hydrogen or C₁₋₃alkyl, and R¹⁰ is phenyl optionally substituted with 1, 2, or 3 substituents selected from C₁₋₄alkyl, halo, C₁₋₄alkoxy, —CF₃, —OCF₃, and —OCHF₂; and
- (f) —S(O)₂R¹¹ wherein R¹¹ is selected from C₁₋₃alkyl, —CH₂-phenyl, furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, 2,4-dimethylisoxazolyl, and phenyl optionally substituted with 1, 2, or 3 substituents selected from C₁₋₄alkyl, halo, C₁₋₄alkoxy, —CF₃, —OCF₃, —OCHF₂, and —CN;

or a pharmaceutically-acceptable salt or solvate or stereoisomer thereof, the process comprising:

(i) reacting a compound of formula (II):

(II)

with a compound of formula (III):

L—X (III)

wherein L is leaving group;

(ii) reacting a compound of formula (VII):

(VIII)

with a compound of formula (XIII):

(XIII)

or (iii) reacting a compound of formula (VI):

(VI)

with a compound of formula (XIV):

(XIV)

to provide a compound of formula (I), or a pharmaceutically-acceptable salt or solvate or stereoisomer thereof.

15. The process of claim 14 wherein the process comprises reacting a compound of formula (VIII):

(VIII)

wherein $R^1$ is isopropyl, with a compound of formula (XIII):

(XIII)

wherein X is —C(O)OCH$_3$, to provide a compound of formula (I) or a pharmaceutically-acceptable salt thereof.

16. A process for preparing a compound of formula (I), (I)

wherein:
$R^1$ is $C_{3-5}$alkyl; and
X is selected from
- (b) —C(O)R$^3$ wherein R$^3$ is selected from:
  phenyl, optionally substituted with 1, 2, or 3 substituents selected from $C_{1-4}$alkyl, halo, $C_{1-4}$alkoxy, —CF$_3$, —OCF$_3$, and —OCHF$_2$, $C_{1-5}$alkyl, $C_{4-5}$cycloalkyl, and
  —(CH$_2$)$_m$-A wherein m is 0 or 1 and A is selected from furanyl, thiophenyl, morpholinyl, tetrahydrofuranyl, pyridinyl, naphthalenyl, pyrrolyl, thiomorpholinyl, pyrrolidinyl, piperidinyl, oxoazetidinyl, thiazolidinyl, 1,1-dioxo isothiazolidinyl, and 2,4-dimethylisoxazolyl;
- (d) —C(O)C(R$^6$R$^7$)R$^8$ wherein R$^6$ is hydrogen or $C_{1-3}$alkyl and R$^7$ is hydrogen, —OH, $C_{1-3}$alkyl, or oxo; or R$^6$ and R$^7$ form —(CH$_2$)$_2$—; and R$^8$ is phenyl or cyclohexyl, wherein phenyl or cyclohexyl are optionally substituted with 1, 2, or 3 substituents selected from $C_{1-4}$alkyl, halo, $C_{1-4}$alkoxy, —CF$_3$, —OCF$_3$, —OCHF$_2$, and —CN; and
- (e) —C(O)C(HR$^9$)OR$^{10}$ wherein R$^9$ is hydrogen or $C_{1-3}$alkyl, and R$^{10}$ is phenyl optionally substituted with 1, 2, or 3 substituents selected from $C_{1-4}$alkyl, halo, $C_{1-4}$alkoxy, —CF$_3$, —OCF$_3$, and —OCHF$_2$;

or a pharmaceutically-acceptable salt or stereoisomer thereof, the process comprising:
reacting a compound of formula (II):

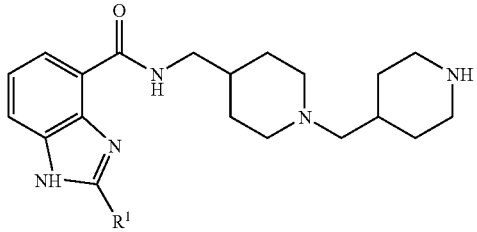
(II)

with a compound of formula (IV):

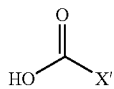
(IV)

wherein X' is selected from $R^3$, $C(R^6R^7)R^8$, and $C(HR^9)OR^{10}$ to provide a compound of formula (I) or a pharmaceutically-acceptable salt or stereoisomer thereof.

17. The product prepared by the process of any one of claims 14 to 16.

18. A compound of formula (II):

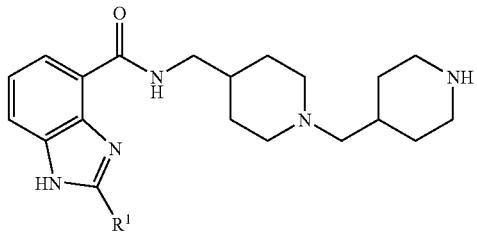
(II)

wherein $R^1$ is $C_{3-5}$alkyl,
or a salt or stereoisomer thereof.

* * * * *

UNITED STATES PATENT AND TRADEMARK OFFICE
CERTIFICATE OF CORRECTION

PATENT NO. : 7,759,363 B2 Page 1 of 1
APPLICATION NO. : 11/439671
DATED : July 20, 2010
INVENTOR(S) : McKinnell et al.

It is certified that error appears in the above-identified patent and that said Letters Patent is hereby corrected as shown below:

In Column 53, at line 54, "$R^{l}$" should be "$R^{1}$".

In Column 53, at line 56, "$-(CH_2)_2-$" should be "$-(CH_2)_n-$".

In Column 54, at line 29, delete "or solvate".

In Column 54, at line 33, "tent-butyl" should be "tert-butyl".

In Column 54, at line 67, "$R^{l}$" should be "$R^{1}$".

In Column 54, at line 67, "tent-butyl" should be "tert-butyl".

In Column 55, at line 50, delete "and solvates".

In Column 55, at line 63, delete "and solvates".

In Column 57, at line 20, "(VII)" should be "(VIII)".

In Column 57, at line 67, delete "or solvate".

Signed and Sealed this

Twenty-first Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,759,363 B2  
APPLICATION NO. : 11/439671  
DATED : July 20, 2010  
INVENTOR(S) : Robert Murray McKinnell et al.

Page 1 of 1

It is certified that error appears in the above-identified patent and that said Letters Patent is hereby corrected as shown below:

In Column 56, at line 66, delete "or solvate".

Signed and Sealed this
Twenty-fifth Day of January, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,759,363 B2 |
| APPLICATION NO. | : 11/439671 |
| DATED | : July 20, 2010 |
| INVENTOR(S) | : Robert Murray McKinnell et al. |

It is certified that error appears in the above-identified patent and that said Letters Patent is hereby corrected as shown below:

In Column 56, at lines 44-45, "or oxo; or $R^6$ and $R^7$ form —$(CH_2)_2$—;" should be "or $R^6$ and $R^7$ taken together form oxo or —$(CH_2)_2$—;".

In Column 58, at lines 58-59, "or oxo; or $R^6$ and $R^7$ form —$(CH_2)_2$—;" should be "or $R^6$ and $R^7$ taken together form oxo or —$(CH_2)_2$—;".

Signed and Sealed this
Twenty-ninth Day of March, 2011

David J. Kappos
*Director of the United States Patent and Trademark Office*